United States Patent
Trombley, III et al.

(10) Patent No.: US 8,852,167 B2
(45) Date of Patent: Oct. 7, 2014

(54) MEDICAL CONNECTOR

(75) Inventors: Frederick W. Trombley, III, Gibsonia, PA (US); Kevin P. Cowan, Allison Park, PA (US); Kraig McEwen, Mars, PA (US); Joseph B. Havrilla, Pittsburgh, PA (US)

(73) Assignee: Bayer Medical Care Inc., Indianola, PA (US)

( * ) Notice: Subject to any disclaimer, the term of this patent is extended or adjusted under 35 U.S.C. 154(b) by 870 days.

(21) Appl. No.: 11/426,348

(22) Filed: Aug. 10, 2006

(65) Prior Publication Data

US 2007/0129705 A1     Jun. 7, 2007

Related U.S. Application Data

(60) Provisional application No. 60/741,146, filed on Dec. 1, 2005.

(51) Int. Cl.
*A61M 25/16* (2006.01)
*A61M 5/00* (2006.01)
*A61M 39/10* (2006.01)

(52) U.S. Cl.
CPC ....... *A61M 39/10* (2013.01); *A61M 2039/1033* (2013.01); *A61M 2039/1038* (2013.01)
USPC ........... 604/533; 604/240; 604/241; 604/243; 604/534; 604/535

(58) Field of Classification Search
USPC ................. 604/167.03, 167.06, 240–243, 604/533–536, 905, 187, 326, 537, 538; 285/333, 390, 392
See application file for complete search history.

(56) References Cited

U.S. PATENT DOCUMENTS

| | | |
|---|---|---|
| 2,019,402 A | 10/1935 | Duffy |
| 3,308,979 A | 3/1967 | Hailes |
| 3,394,954 A | 7/1968 | Sarns |

(Continued)

FOREIGN PATENT DOCUMENTS

| | | |
|---|---|---|
| EP | 0028198 | 5/1981 |
| EP | 0309426 | 3/1989 |

(Continued)

OTHER PUBLICATIONS

"High Flow Check Valves, Large Bore Shielded Connectors" Resenex Corporation.

*Primary Examiner* — Emily Schmidt
*Assistant Examiner* — Lauren M Peng
(74) *Attorney, Agent, or Firm* — David Schramm

(57) ABSTRACT

A medical connector includes a body defining a lumen for fluid flow through the medical connector. The medical connector includes a luer member and an annular member disposed about the luer member. The annular member includes internal and/or external engagement structures. The medical connector may be provided on the outlet of a syringe or on a catheter. A fluid path is disclosed including a first section and a second section. The first and second sections may each include a medical connector to provide a removable connection with a syringe and a catheter, respectively. The medical connector may provide a removable connection between the first and second sections. A fluid delivery system is disclosed including an injector, a syringe operatively associated with the injector, and a fluid path connecting the syringe and a source of injection. The medical connector may provide a removable connection between the syringe and fluid path.

14 Claims, 27 Drawing Sheets

(56) References Cited

U.S. PATENT DOCUMENTS

| | | | |
|---|---|---|---|
| 3,470,929 A | 10/1969 | Thornton | |
| 3,588,149 A | 6/1971 | Demler | |
| 3,727,613 A * | 4/1973 | Sorenson et al. | 604/165.02 |
| 3,768,476 A | 10/1973 | Raitto | |
| 3,876,319 A | 4/1975 | Meyer | |
| 3,976,311 A | 8/1976 | Spendlove | |
| 4,022,205 A | 5/1977 | Tenczar | |
| 4,030,494 A | 6/1977 | Tenczar | |
| 4,046,145 A | 9/1977 | Choski | |
| 4,051,850 A * | 10/1977 | Tischlinger | 604/202 |
| 4,161,178 A | 7/1979 | Genese | |
| 4,161,949 A | 7/1979 | Thanawalla | |
| 4,187,848 A * | 2/1980 | Taylor | 604/243 |
| 4,266,815 A * | 5/1981 | Cross | 285/330 |
| 4,338,933 A | 7/1982 | Bayard et al. | |
| 4,342,337 A | 8/1982 | Underwood | |
| 4,344,435 A | 8/1982 | Aubin | |
| 4,354,490 A | 10/1982 | Rogers | |
| 4,372,336 A | 2/1983 | Cornell et al. | |
| 4,433,973 A | 2/1984 | Kurtz et al. | |
| 4,439,188 A | 3/1984 | Dennehey et al. | |
| 4,508,367 A | 4/1985 | Oreopoulos et al. | |
| 4,540,405 A * | 9/1985 | Miller et al. | 604/232 |
| 4,551,146 A | 11/1985 | Rogers | |
| 4,610,469 A | 9/1986 | Wolff-Mooij | |
| 4,624,664 A * | 11/1986 | Peluso et al. | 604/256 |
| 4,629,455 A * | 12/1986 | Kanno | 604/241 |
| 4,636,204 A | 1/1987 | Christopherson et al. | |
| 4,642,091 A | 2/1987 | Richmond | |
| 4,798,404 A | 1/1989 | Iyanicki | |
| 4,911,697 A | 3/1990 | Kerwin | |
| RE33,585 E | 5/1991 | Haber et al. | |
| 5,105,844 A | 4/1992 | King, Sr. | |
| 5,176,415 A | 1/1993 | Choksi | |
| 5,286,067 A | 2/1994 | Choksi | |
| 5,452,748 A | 9/1995 | Simmons et al. | |
| 5,460,609 A | 10/1995 | O'Donnell | |
| 5,464,399 A * | 11/1995 | Boettger | 604/533 |
| 5,503,187 A | 4/1996 | Simmons et al. | |
| 5,515,851 A | 5/1996 | Goldstein | |
| 5,573,515 A | 11/1996 | Wilson et al. | |
| 5,634,903 A * | 6/1997 | Kurose et al. | 604/110 |
| 5,676,406 A | 10/1997 | Simmons et al. | |
| 5,800,397 A | 9/1998 | Wilson et al. | |
| 5,840,026 A | 11/1998 | Uber, III et al. | |
| 5,906,402 A | 5/1999 | Simmons et al. | |
| 5,916,165 A | 6/1999 | Duchon | |
| 5,924,584 A * | 7/1999 | Hellstrom et al. | 215/247 |
| 6,096,011 A | 8/2000 | Trombley, III et al. | |
| 6,283,182 B1 | 9/2001 | Fedeli | |
| 6,440,107 B1 | 8/2002 | Trombley, III et al. | |
| 6,569,118 B2 * | 5/2003 | Johnson et al. | 604/164.04 |
| 6,672,244 B1 | 1/2004 | Martin | |
| 6,840,291 B2 * | 1/2005 | Caizza et al. | 141/25 |
| 7,563,249 B2 | 7/2009 | Schriver | |
| 7,611,503 B2 | 11/2009 | Spohn | |
| 2001/0016703 A1* | 8/2001 | Wironen et al. | 604/89 |
| 2002/0014429 A1 | 2/2002 | Johnson | |
| 2002/0147429 A1* | 10/2002 | Cowan et al. | 604/187 |
| 2002/0173753 A1* | 11/2002 | Caizza et al. | 604/241 |
| 2003/0151256 A1 | 8/2003 | Guala | |
| 2004/0068248 A1 | 4/2004 | Mooney et al. | |
| 2004/0210199 A1 | 10/2004 | Atterbury et al. | |
| 2004/0254533 A1 | 12/2004 | Schriver et al. | |
| 2005/0230575 A1 | 10/2005 | Zelenski et al. | |
| 2005/0234428 A1 | 10/2005 | Spohn et al. | |
| 2005/0251096 A1 | 11/2005 | Armstrong | |
| 2007/0123829 A1 | 5/2007 | Atterbury et al. | |
| 2007/0129705 A1 | 6/2007 | Trombley, III et al. | |

FOREIGN PATENT DOCUMENTS

| | | |
|---|---|---|
| EP | 0349745 | 1/1990 |
| GB | 2040379 | 8/1980 |
| JP | 5184686 | 7/1993 |
| JP | 5272685 | 10/1993 |
| JP | 6165820 | 6/1994 |
| JP | 2003176892 | 6/2003 |
| WO | 2005/049110 | 6/2005 |

* cited by examiner

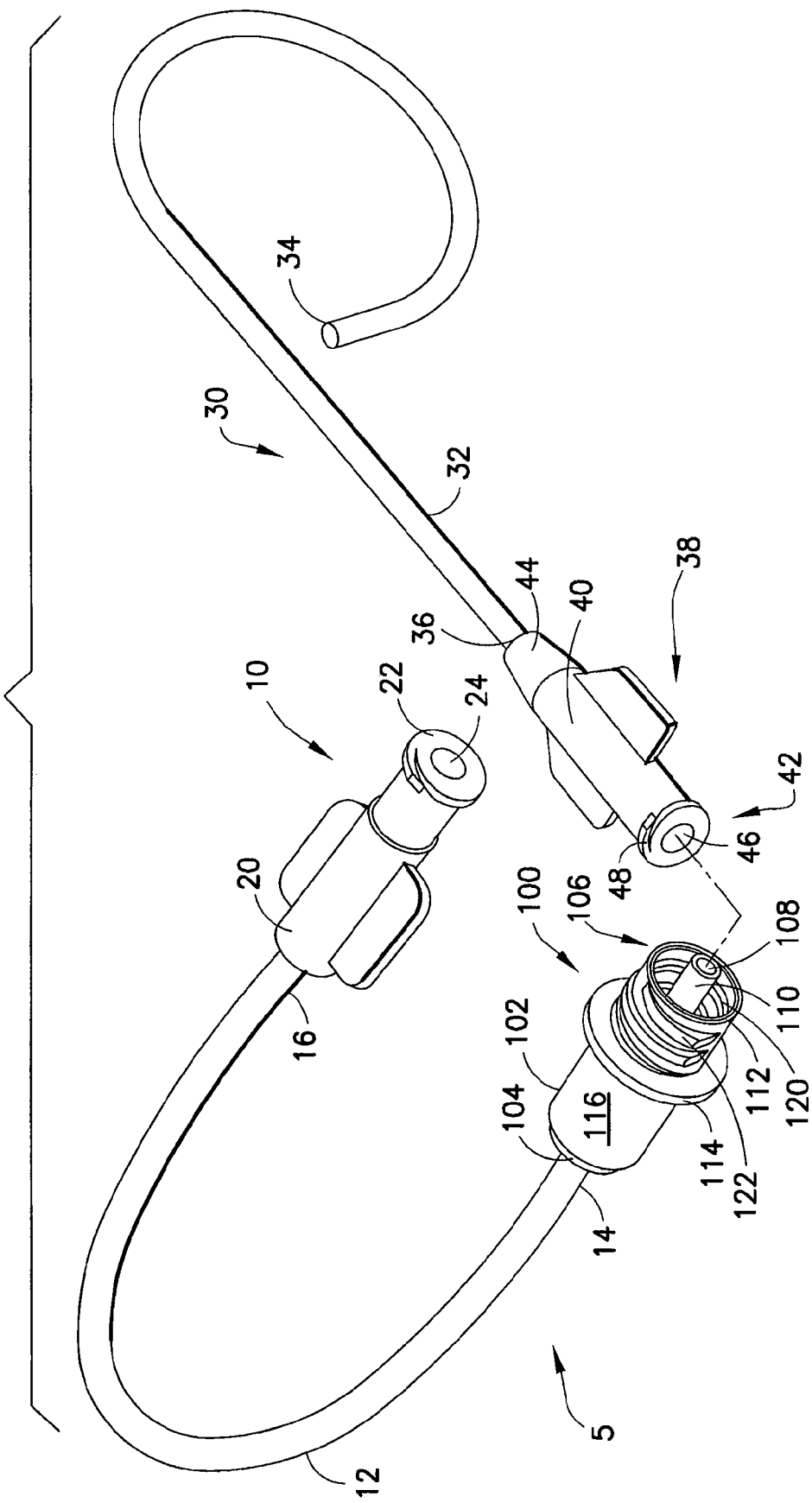

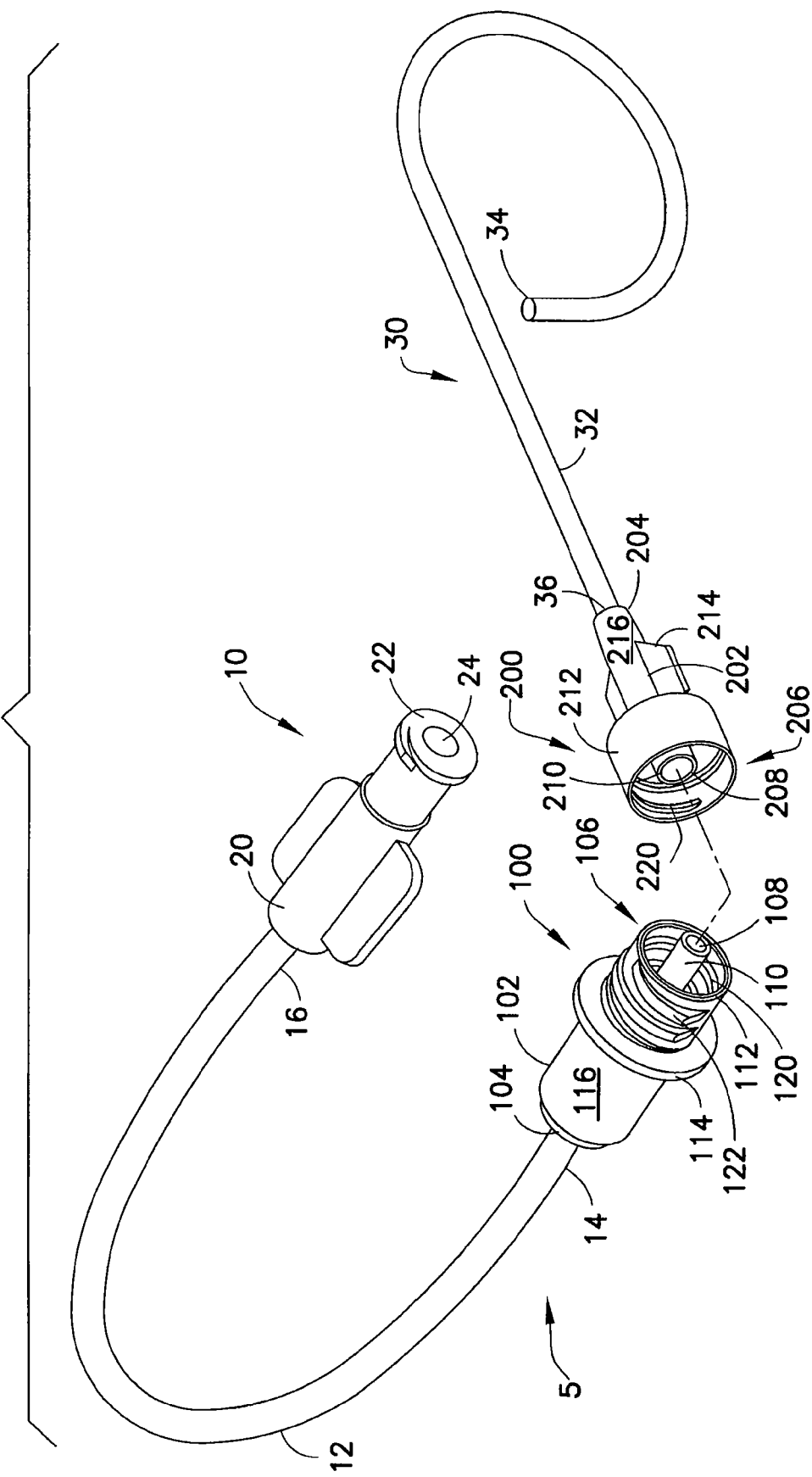

MEDICAL CONNECTOR

BACKGROUND OF THE INVENTION

1. Field of the Invention

The present invention relates generally to fluid delivery systems for supplying fluids during medical diagnostic and therapeutic procedures and, further, to medical connectors for use with such fluid delivery systems and fluid paths used in fluid delivery systems.

2. Description of Related Art

In many medical diagnostic and therapeutic procedures, a medical practitioner such as a physician injects a patient with a fluid. In recent years, a number of injector-actuated syringes and powered injectors for pressurized injection of fluids, such as contrast media, have been developed for use in procedures such as angiography, computed tomography, ultrasound, and NMR/MRI. In general, these powered injectors are designed to deliver a preset amount of contrast media at a preset flow rate.

Angiography is used in the detection and treatment of abnormalities or restrictions in blood vessels. In an angiographic procedure, a radiographic image of a vascular structure is obtained through the use of a radiographic contrast medium, sometimes referred to simply as contrast, which is injected through a catheter. The vascular structures in fluid connection with the vein or artery in which the contrast is injected are filled with contrast. X-rays passing through the region of interest are absorbed by the contrast, causing a radiographic outline or image of blood vessels containing the contrast. The resulting images can be displayed on, for example, a video monitor and recorded.

In a typical angiographic procedure, the medical practitioner places a cardiac catheter into a vein or artery. The catheter is connected to either a manual or to an automatic contrast injection mechanism. A typical manual contrast injection mechanism includes a syringe in fluid connection with a catheter connection. The fluid path also includes, for example, a source of contrast, a source of flushing fluid, typically saline, and a pressure transducer to measure patient blood pressure. In a typical system, the source of contrast is connected to the fluid path via a valve, for example, a three-way stopcock. The source of saline and the pressure transducer may also be connected to the fluid path via additional valves. The operator of the manual system controls the syringe and each of the valves to draw saline or contrast into the syringe and to inject the contrast or saline into the patient through the catheter connection. The pressure transducers used in such procedures are extremely sensitive to even moderately high pressures generated during activation of the syringe, so the operator must close a valve to isolate the pressure transducer from the fluid path when the syringe is activated to prevent damage to the pressure transducer. While the syringe is not activated, the valve is usually open to monitor patient blood pressure.

The operator of the syringe may adjust the flow rate and volume of injection by altering the force applied to the plunger of the syringe. Manual sources of fluid pressure and flow used in medical applications such as syringes and manifolds thus typically require operator effort that provides feedback of the fluid pressure/flow generated to the operator. The feedback is desirable, but the operator effort often leads to fatigue. Thus, fluid pressure and flow may vary depending on the operator's strength and technique.

Automatic contrast injection mechanisms typically include a syringe connected to a powered injector having, for example, a powered linear actuator. Typically, an operator enters settings into an electronic control system of the powered injector for a fixed volume of contrast and a fixed rate of injection. In many systems, there is no interactive control between the operator and the powered injector, except to start or stop the injection. A change in flow rate in such systems occurs by stopping the machine and resetting the injection parameters. Automation of angiographic procedures using powered injectors is discussed, for example, in U.S. Pat. Nos. 5,460,609; 5,573,515; and 5,800,397.

U.S. Pat. No. 5,800,397 discloses an angiographic injector system having high pressure and low pressure systems. The high pressure system includes a motor-driven injector pump to deliver radiographic contrast under high pressure to a catheter. The low pressure system includes, among other things, a pressure transducer to measure blood pressure and a pump to deliver a saline solution to the patient as well as to aspirate waste fluid. A manifold is connected to the syringe pump, the low-pressure system, and the patient catheter. A flow valve associated with the manifold is normally maintained in a first state connecting the low pressure system to the catheter through the manifold, and disconnecting the high pressure system from the catheter and the low pressure system. When pressure from the syringe pump reaches a predetermined and set level, the valve switches to a second state connecting the high pressure system/syringe pump to the catheter, while disconnecting the low pressure system from the catheter and from the high pressure system. In this manner, the pressure transducer is protected from high pressures. However, compliance in the system components, for example, expansion of the syringe, tubing, and other components under pressure, using such a manifold system can lead to a less than optimal injection bolus. Moreover, the arrangement of the system components of U.S. Pat. No. 5,800,397 results in relatively large amounts of wasted contrast and/or undesirable injection of an excessive amount of contrast when the low pressure, typically saline, system is used.

The injector system of U.S. Pat. No. 5,800,397 also includes a handheld remote control connected to a console. The control includes saline push button switches and a flow rate control lever or trigger. By progressive squeezing of the control trigger, the user provides a command signal to the console to provide a continuously variable injection rate corresponding to the degree of depression of the control trigger. U.S. Pat. No. 5,916,165 discloses a handheld pneumatic controller for producing a variable control signal to control a rate of fluid dispersement to the patient in an angiographic system. U.S. Pat. No. 5,515,851 discloses an angiographic system with a finger activated control pad to regulate the injection of fluids.

U.S. Pat. No. 5,840,026 discloses an injection system in which an electronic control system is connected to the fluid delivery system and a tactile feedback control unit. In one embodiment, the tactile feedback control unit includes a disposable syringe that is located within a durable/reusable cradle and is in fluid connection with the fluid being delivered to the patient. The cradle is electrically connected to the electronic control system and is physically connected to a sliding potentiometer that is driven by the plunger of a disposable syringe. During use of the injection system of U.S. Pat. No. 5,840,026, the operator holds the cradle and syringe and, as the operator depresses the sliding potentiometer/syringe piston assembly, the plunger is moved forward, displacing fluid toward the patient and creating pressure in the syringe. A sliding potentiometer tracks the position of the syringe plunger. The electronic control system controls the contrast delivery system to inject an amount of fluid into the patient based on the change in position of the plunger. As the fluid is injected, the pressure the operator feels in his or her hand is proportional to the actual pressure produced by the contrast delivery system. The force required to move the piston provides the operator with tactile feedback on the pressure in the system. The operator is able to use this feedback to ensure the safety of the injection procedure. Unlike the case of a manual injection system, the injection system of U.S. Pat. No. 5,840,026 does not require the operator to develop the system pressure and flow rate. The operator develops a smaller, manually applied pressure that corresponds to or is proportional to the system pressure. The required manual power output, that is pressure X flow rate, is decreased as compared to manual systems, whereas the tactile feedback associated therewith is retained.

Medical connectors are commonly used in fluid delivery systems, as described above, for establishing the various fluid connections necessary in the system. For example, the indwelling cardiac catheter typically comprises a medical connector for connecting the catheter to medical tubing which associates the catheter to the source of contrast injection fluid, typically a syringe, and the source of saline. A typical catheter connector includes a female luer with a threaded tip adapted to receive a male luer surrounded by an annular member including corresponding threads on an inside surface thereof. Traditional medical connectors are also used at other fluid connection points in fluid delivery systems, such as to make connections in the low pressure system used to deliver saline to the catheter and, thus, to the patient. Such traditional medical connectors typically include either a threaded connection or a friction fit coupling to connect sections of tubing or other tubular devices such as needles and syringes. In a threaded connection, at least one part of the medical connector includes threads and the other part includes threads or lugs that are received in the threads. One part is turned relative to the other to make the connection. This type of medical connector is prone to unintentional decoupling. In a friction fit coupling, a male fitting having a frustoconical shape is typically inserted into a female fitting having a frustoconical-shaped receiving cavity. Opposing conical surfaces on the female and male fittings come into contact with each other and form a friction fit. This type of medical connector is also susceptible to accidental decoupling.

In view of the number of fluid connections required in, for example, an angiographic fluid delivery system, it is important to ensure that the medical connectors remain connected, particularly those in the high pressure system for the safety of attending medical personnel and the patient. In particular, due to the high pressures associated with angiographic contrast injection procedures, it is important to have, for example, a secure connection between the indwelling catheter and the fluid delivery tubing (i.e., fluid path) connected to the contrast delivery syringe. An accidental disconnection of the catheter can lead to many serious problems including loss of blood and contamination of the surroundings and/or medical personnel and the cessation of fluid delivery to the patient.

Typical "standard", threaded or friction fit, medical connectors are often limited to use at relatively low pressures. Angiographic procedures often require the delivery of contrast to a patient at pressures of approximately 300 psi and higher. Although "high pressure" medical connectors are known in the medical field for use with high pressure medical tubing, such high-pressure medical connectors remain susceptible to ruptures and other problems and are not typically designed to be aseptic. Moreover, it is common to use fluid delivery systems to deliver fluids to patients at both low and high pressures. However, typical specially-designed high pressure medical connectors are not adapted to mate with both other corresponding high pressure connectors and conventional or standard "low pressure" medical connectors, thus limiting their utility as a "multi-purpose" connector.

Accordingly, a need exists for a secure fluid delivery system and fluid path that includes medical connectors that are suitable for use at relatively high pressures and which can accept both standard or conventional medical connectors and medical connectors specifically adapted for use at high pressures.

SUMMARY OF THE INVENTION

Generally, one aspect of the invention disclosed herein relates to a medical connector comprising a body defining a lumen for fluid flow through the medical connector and comprising a luer member and an annular member disposed about the luer member. The annular member may comprise internal or external engagement structure or both internal and external engagement structure. The annular member may be coaxially disposed about the luer member. The annular member may be rotationally connected to the connector body. Additionally, the luer member may be recessed within the annular member.

In one embodiment, the annular member may comprise both internal and external engagement structure, for example, in the form of threads. In this embodiment, the annular member via the internal and external threads is adapted to cooperate with either an externally threaded luer connector or an internally threaded luer connector. The luer member may comprise either a male luer member or a female luer member. Additionally, in this embodiment, the luer member may comprise internal or external engagement structure, for example, in the form of threads.

In another embodiment, the annular member may comprise either internal or external engagement structure, for example, in the form of threads. In this embodiment, the luer member may also comprise internal or external engagement structure, for example, in the form of threads.

In another aspect, the invention relates to a syringe comprising a syringe body comprising a cylindrical main portion, a conical portion connected to the main body portion, and a discharge outlet connected to the conical portion. A medical connector is disposed at the end of the discharge outlet and comprises a body defining a lumen for fluid flow through the medical connector. The medical connector body further comprises a luer member and an annular member disposed about the luer member. The annular member may comprise internal or external engagement structure or both internal and external engagement structure. The syringe body and medical connector body may be formed integrally.

In a further aspect, the invention relates to a catheter comprising an elongated flexible and tubular catheter body having a distal end and a proximal end. A medical connector is disposed at the proximal end of the catheter body and comprises a body defining a lumen for fluid flow through the medical connector. The medical connector body further comprises a luer member and an annular member disposed about the luer member. The annular member may comprise internal or external engagement structure or both internal and external engagement structure.

In a still further aspect, the invention relates to a fluid path for use in a fluid delivery system. The fluid path generally comprises a syringe, a first section adapted for removable connection with the syringe and to a source of injection fluid to be loaded into the syringe, and a second section adapted for removable connection with the first section and for removable connection with a catheter for interfacing with a patient. The first section and second section each comprise a medical connector to provide the removable connection with the syringe and catheter, respectively. At least one of the medical connectors comprises a body defining a lumen for fluid flow through the medical connector. The body further comprises a luer member and an annular member disposed about the luer member. The annular member may comprise internal or external engagement structure or both internal and external engagement structure.

In another embodiment of the fluid path, the fluid path comprises a syringe, a first section adapted for removable connection with the syringe and to a source of injection fluid to be loaded into the syringe, and a second section adapted for removable connection with the first section and for removable connection with a catheter for interfacing with a patient. A medical connector provides the removable connection between the first section and second section, and comprises a medical connector comprising a body defining a lumen for fluid flow through the medical connector. The medical connector body further comprises a luer member and an annular member disposed about the luer member. The annular member may comprise internal or external engagement structure or both internal and external engagement structure.

Moreover, the invention relates to a fluid delivery system comprising a powered injector, a syringe in operative connection with the powered injector, and a fluid path adapted for removable connection with the syringe and to a source of injection fluid to be loaded into the syringe. A medical connector provides the removable connection between the syringe and fluid path, and comprises a medical connector comprising a body defining a lumen for fluid flow through the medical connector. The medical connector body further comprises a luer member and an annular member disposed about the luer member. The annular member may comprise internal or external engagement structure or both internal and external engagement structure.

In the fluid delivery system, the fluid path may be further adapted for removable connection with a catheter for delivering the injection fluid to a patient. The removable connection between the fluid path and catheter may be provided by an additional one of the medical connector. The annular member of the additional one of the medical connector may comprise both internal and external engagement structure, for example, in the form of threads. The luer member of the additional one of the medical connector may comprise either a male luer member or a female luer member. The luer member of the additional one of the medical connector may also comprise internal or external engagement structure, for example in the form of threads. Additionally, the luer member of the additional one of the medical connector may comprise internal or external engagement structure, for example, in the form of threads. Further, the luer member of the additional one of the medical connector may be recessed within the annular member. Furthermore, the annular member of the additional one of the medical connector may be rotationally connected to the connector body.

In still another aspect, the invention relates to a medical connector assembly, comprising a first connector and a second connector. The first connector comprises a body defining a lumen for fluid flow through the first connector. The first connector body comprises a first luer member and a first annular member disposed about the first luer member. The first annular member comprises internal and external engagement structure, such as threads. The second connector also comprises a body defining a lumen for fluid flow through the second connector. The second connector body comprises a second luer member adapted for engagement with the first luer member and a second annular member disposed about the second luer member and adapted to cooperate with the first annular member. The second annular member comprises internal or external engagement structure, for example, threads, for engaging the corresponding engagement structure, for example, threads, disposed on the first annular member.

The first luer member may comprise a male luer member and the second luer member may comprise a female luer member. The male first luer member may comprise external engagement structure, for example, threads, and the female second luer member may comprise internal engagement structure, for example, threads. Alternatively, the first luer member may comprise a female luer member and the second luer member may comprise a male luer member. The female first luer member may comprise internal engagement structure, for example, threads, and the male second luer member may comprise external engagement structure, for example, threads.

The first luer member and/or the second luer member may be recessed within the respective first and second annular members in the medical connector assembly. Additionally, the first annular member and/or the second annular member may be rotationally connected to the respective first and second connector bodies in the medical connector assembly.

Further details and advantages of the present invention will become clear upon reading the following detailed description in conjunction with the accompanying drawings, wherein like reference numerals identify like parts throughout.

BRIEF DESCRIPTION OF THE DRAWINGS

FIG. 3A is a perspective view showing the medical connector of FIG. 1 associated with a catheter having a female luer connector;

FIG. 7A is a perspective view showing the medical connector device of FIG. 1 associated with a catheter comprising a medical connector according to another aspect of the invention and adapted to mate with the medical connector of FIG. 1;

DETAILED DESCRIPTION OF THE PRESENT INVENTION

Figure 1:
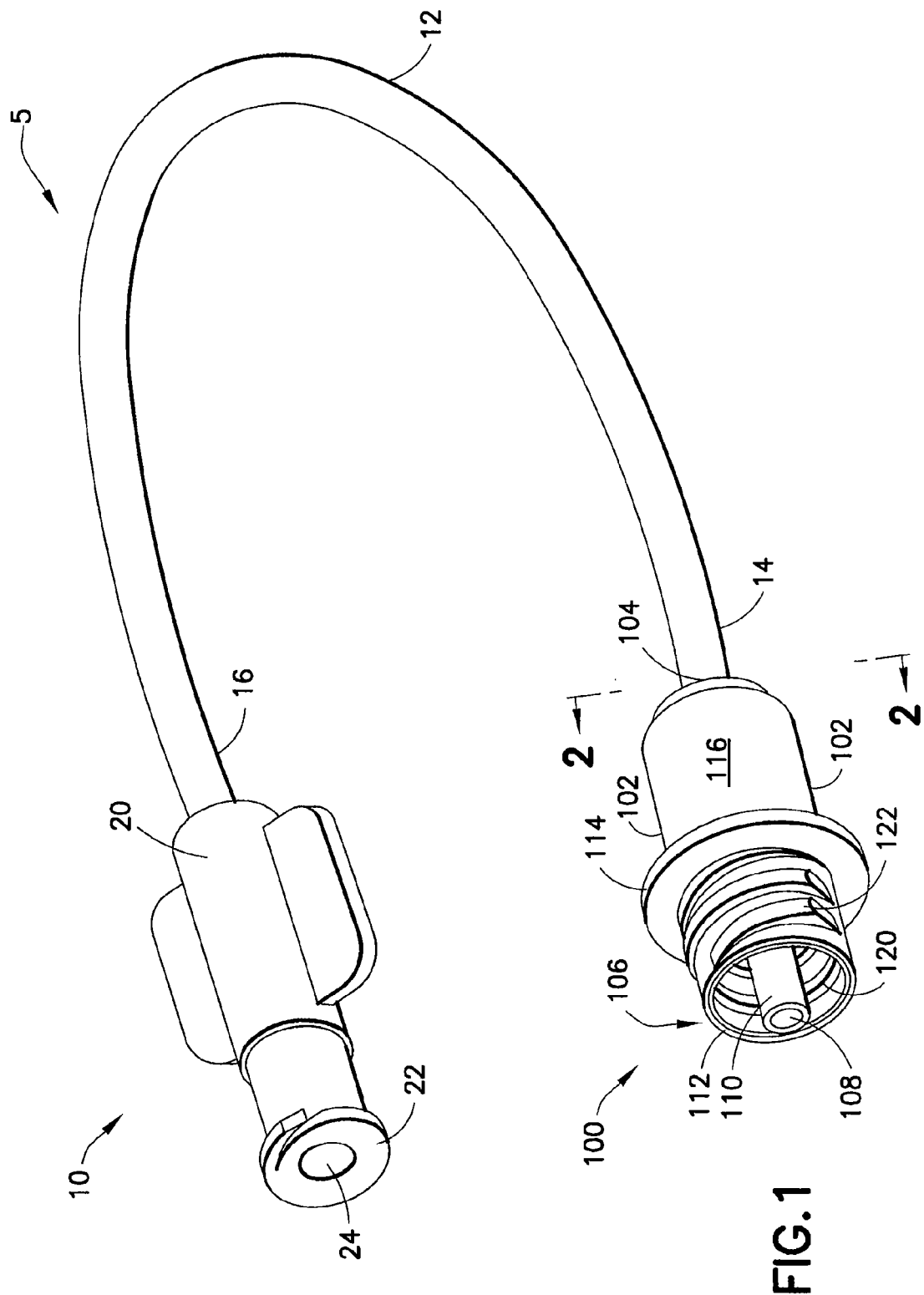
FIG. 1 is a perspective view of a medical connector according to one aspect of the invention provided as part of a medical connector device.

For purposes of the description hereinafter, spatial orientation terms, if used, shall relate to the embodiment of the invention as it is oriented in the accompanying drawing figures. However, it is to be understood that the present invention may assume many alternative variations and embodiments except where expressly specified to the contrary. It is also to be understood that the specific devices and embodiments illustrated in the accompanying drawing figures and described herein are simply exemplary embodiments of the invention, and wherein like elements are designated with like reference numerals throughout.

Figure 2:
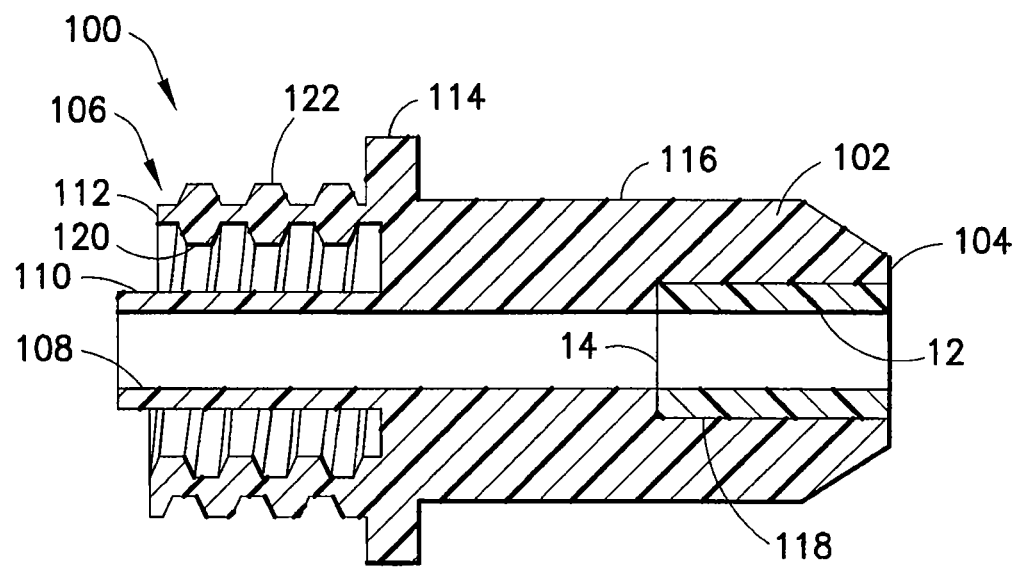
FIG. 2 is a cross-sectional view taken along line 2-2 in FIG. 1.

Referring to FIGS. 1 and 2, a medical connector device 5 is generally shown. A medical connector 100 in accordance with one aspect of the invention forms one connecting end of connector device 5, while a standard or conventional female luer connector 10 may form the other connecting end of connector device 5, as an example. Connector device 5 is typically used to complete various fluid connections within a fluid delivery system, such as a fluid delivery system used to deliver contrast media to a patient in an angiographic procedure. For example, connector device 5 may be used in such systems to connect an indwelling cardiac catheter to a fluid path ultimately connected to a pressurizing syringe. In a manual contrast fluid delivery system, connector device 5 may be used to connect the indwelling cardiac catheter directly to the pressurizing syringe. While the foregoing are specific end use applications for connector device 5, connector device 5 may be used to complete fluid connections in virtually any medical fluid delivery application, including therapeutic or diagnostic applications, or as part of blood collection or bodily fluid collection sets. Accordingly, connector device 5 has applications in the medical field generally for completing necessary fluid connections between fluid delivery apparatus and/or medical tubing, and between bodily fluid collection apparatus and/or medical tubing. Connector device 5 is used as a vehicle to describe medical connector 100 which forms one aspect of the invention described herein.

As illustrated in FIGS. 1 and 2, medical tubing 12 fluidly connects luer connector 10 and medical connector 100. Tubing 12 extends between medical connector 100 and luer connector 10, and typically has one end adhesively secured within medical connector 100 and an opposing end secured within luer connector 10 by a suitable medical grade adhesive. As an alternative, tubing 12 may be formed integrally with the bodies of medical connector 100 and luer connector 10 if desired. Tubing 12 may be either high pressure or low pressure tubing and may be conventional in the medical field. Tubing 12 comprises a first end 14 connected to medical connector 100 and a second end 16 connected to luer connector 10. Tubing 12 may have any suitable length, and the length of tubing 12 may be varied as necessary to suit the intended fluid delivery or fluid collection procedure. As indicated, the second end 16 of tubing 12 is connected to luer connector 10. Luer connector 10 may be a conventional or standard "female" luer connector and comprise a body 20 having flange 22 for forming connections, typically threaded, with a mating "male" luer connector or, possibly, medical connector 100 of another connector device 5. Female luer body 20 defines a lumen 24 for receiving a mating male luer and for fluid flow through body 20 as is known in the art.

Medical connector 100 comprises a typically unitary body 102 having a first or proximal end 104 and a second or distal end 106. The first end 14 of tubing 12 is connected to the first end 104 of connector body 102 while the second end 106 is adapted to engage and complete a fluid connection with another medical component such as a syringe or catheter or even another connector device 5 as examples. Connector body 102 defines a lumen 108 for fluid flow through medical connector 100. Connector body 102 is further formed with a luer member 110 which extends distally from the connector body 102 and which, at least in part, defines or forms lumen 108. Luer member 110 is illustrated as a male luer member, but may also be formed as a female luer member, as shown in FIG. 9B discussed herein. Connector body 102 is further formed with an annular member 112 disposed about luer member 110. Annular member 112 may be coaxially disposed about luer member 110, and luer member 110 typically extends or projects distally outward from annular member 112 in the embodiment of medical connector 100 shown in FIGS. 1 and 2. As shown in FIG. 10 discussed herein, luer member 110 may also be recessed within annular member 112 to improve the aseptic characteristics of medical connector 100. Connector body 102 may further be formed with a circumferential or perimetric flange 114 extending about connector body 102 proximal or rearward of annular member 112. Flange 114 provides an engagement surface or structure for the user of medical connector 100, and which may be used to restrict or inhibit the user from contacting annular member 112 when the user attempts to connect the medical connector 100 to another component. In particular, when the user of medical connector 100 is ready to connect the medical connector 100 to another component, the user typically grasps an outer surface 116 of connector body 102 between his or her thumb and index finger. The user's thumb and index finger is prevented or restricted from contacting annular member 112 due to the location of flange 114. Flange 114 further provides a surface against which the user may apply pressure to connect the medical connector 100 to another medical component, such as a syringe or catheter as examples. Lumen 108, as shown in particular in FIG. 2, defines a recessed area 118 for accepting the first end 14 of tubing 12, with tubing 12 typically adhesively secured within recessed area 118 by a suitable medical grade adhesive, as indicated previously.

Figure 2A:
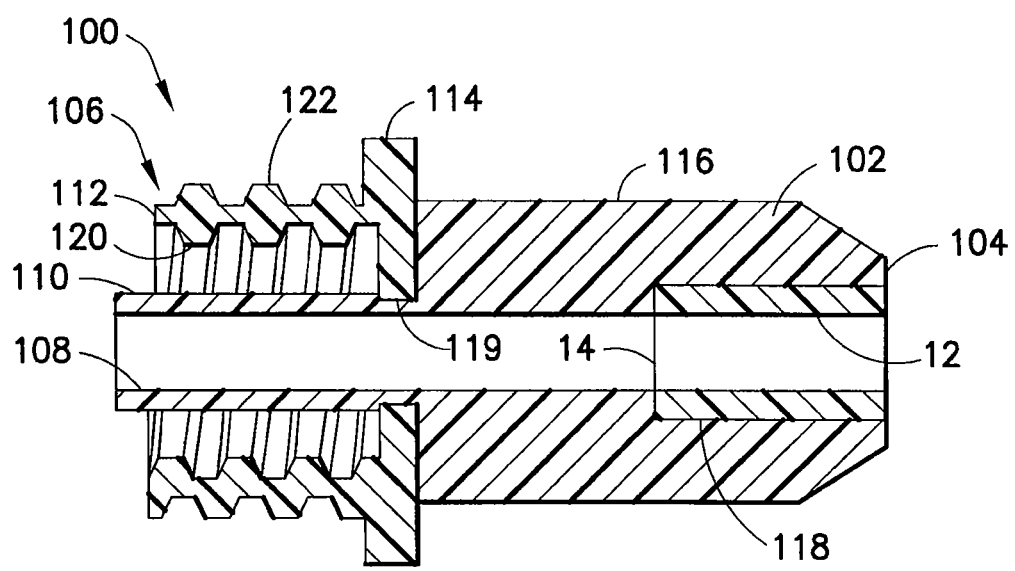
FIG. 2A is a cross-sectional view of the medical connector shown in FIG. 1 further comprising a rotatable annular member.

In a variation of medical connector 100 shown in FIG. 2A, flange 114 and annular member 112 are formed integrally and are rotationally connected to connector body 102. The rotational connection is achieved by locating flange 114 in a circumferential recess 119 defined in connector body 102 so that flange 114 and annular member 112 may freely rotate or swivel relative to connector body 102. The rotation of flange 114 relative to connector body 102 allows for easier connection of annular member 112 to a mating threaded component by allowing annular member 112 to thread onto or into such a mating component while connector body 102 remains stationary. As a result, tubing 12 is not twisted or "kinked" during the connection process as could occur with medical connector 100 shown in FIG. 2, wherein flange 114 and annular member 112 are integral with connector body 102.

Referring again to FIGS. 1 and 2, annular member 112 is typically formed with internal and external engagement structure 120, 122, respectively, that are adapted to engage mating structure of another medical component to form the connection between medical connector 100 and such other medical component. In the embodiment of medical connector 100 shown in FIGS. 1 and 2, the internal and external engagement structures 120, 122 comprise threads. However, the internal and external engagement structures 120, 122 (hereinafter "internal threads" and "external threads", respectively) could also be formed to provide a permanent connection between medical connector 100 and the mating medical component, such as being formed as a barb-type structure that engages a mating recess in the mating medical component and thereafter prevents decoupling of medical connector 100 from the mating medical component. Additionally, it will be appreciated that suitably equivalent mechanical connecting structure to conventional threads may be substituted for the threads shown in FIGS. 1 and 2, or in any of the Figures associated with this disclosure. One example of such generally equivalent structure is bayonet projections (not shown) which may be provided in place of internal and external threads 120, 122 and which are adapted to mate with corresponding sockets in the mating medical component.

Due to the presence of internal engagement structure or internal threads 120 within annular member 112, medical connector 100 is adapted to connect with a standard or conventional externally-threaded "female" luer connector such as luer connector 10 of another connector device 5. Additionally, due to the additional presence of external engagement structure or external threads 122 on annular member 112, medical connector 100 is also adapted to connect with a mating internally-threaded mating medical component, such as mating medical connector 200 discussed herein or even another medical connector 100 with a suitably sized (e.g., enlarged) annular member 112 and appropriately configured luer member 110, (see FIG. 16 discussed herein). Accordingly, medical connector 100 is adapted to engage with both externally-threaded and internally-threaded components due to the double-threaded configuration of annular member 112. Moreover, as will be appreciated by those skilled in the art, luer member 110 in medical connector 100 may be provided as a "male" luer member adapted to engage a receiving "female" luer or lumen in the mating medical component. This configuration may also be reversed in accordance with this invention, wherein luer member 110 is formed as a female luer member adapted to receive a male luer disposed on the mating medical component. Both possible mating configurations relating to luer member 110 of medical connector 100 are described herein in connection with respect to FIGS. 9A-9B.

Figure 3B:
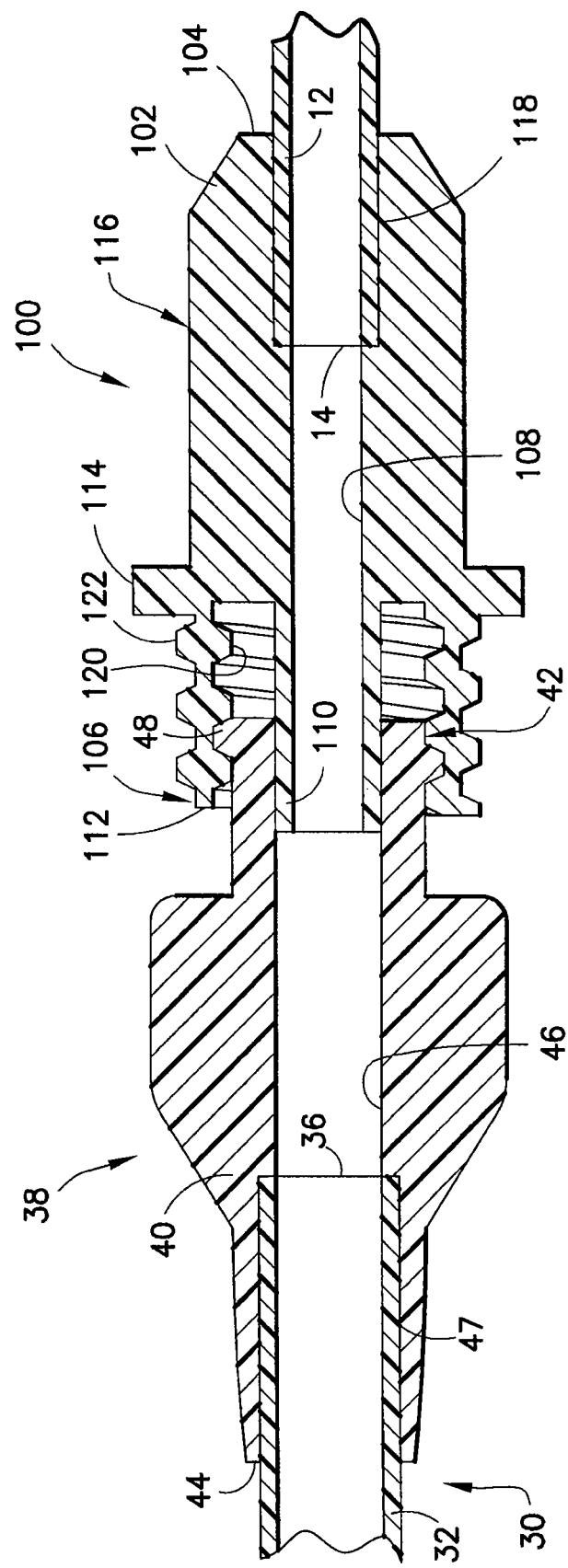
FIG. 3B is a cross-sectional view showing the medical connector of FIG. 1 engaged with the catheter of FIG. 3A.

Referring further to FIGS. 3A and 3B, connector device 5 and medical connector 100 are shown interfacing with a catheter 30 as a representative mating medical component. Catheter 30 may be conventional in the medical field such as a Medrad®, Inc. Vanguard DX™ Angiographic Catheter as disclosed in U.S. Provisional Patent Application No. 60/520,071 filed Nov. 15, 2003 and PCT Patent Application No. PCT/US2004/038093, assigned to the same assignee as the present application and which is incorporated herein by reference in its entirety. Generally, catheter 30 comprises an elongated, flexible, and tubular body 32 having a distal end 34 and a proximal end 36. Catheter body 32 is intended to be inserted into a vein or artery of patient in a conventional manner, as would occur in preparation for an angiographic procedure, as an example. Distal end 34 of catheter body 32 is situated in the blood vessel of the patient while proximal end 36 resides outside the patient's body 36 and is used as the connection point for connecting catheter 30 to one or more sources of fluid to be injected into the patient. Catheter body 32 may have any suitable size or shape for the intended fluid delivery or fluid removal procedure such as 4 French and 5 French. A luer connector 38 is attached to the proximal end 36 of catheter body 32 to form a mating connection with another medical component such as connector device 5. Luer connector 38 is shown as a standard or conventional female luer connector, much like luer connector 10 discussed previously. Luer connector 38 comprises a body 40 having a first or distal end 42 and a second proximal end 44. Luer body 40 defines a lumen 46 for fluid flow through the luer body 40. As shown in FIG. 3B, proximal end 36 of catheter body 32 is secured within the proximal end 44 of luer body 40 which is situated or resides outside the patient's body when catheter 30 is in use. The proximal end 36 of catheter body 32 may be received within a recessed area 47 defined in luer body 40 by a suitable medical grade adhesive. Alternatively, luer body 40 and catheter body 32 may be formed integrally. Additionally, luer body 40 typically comprises an externally-threaded flange 48 at distal end 42 for forming a mating connection with medical connector 100.

Figure 13:
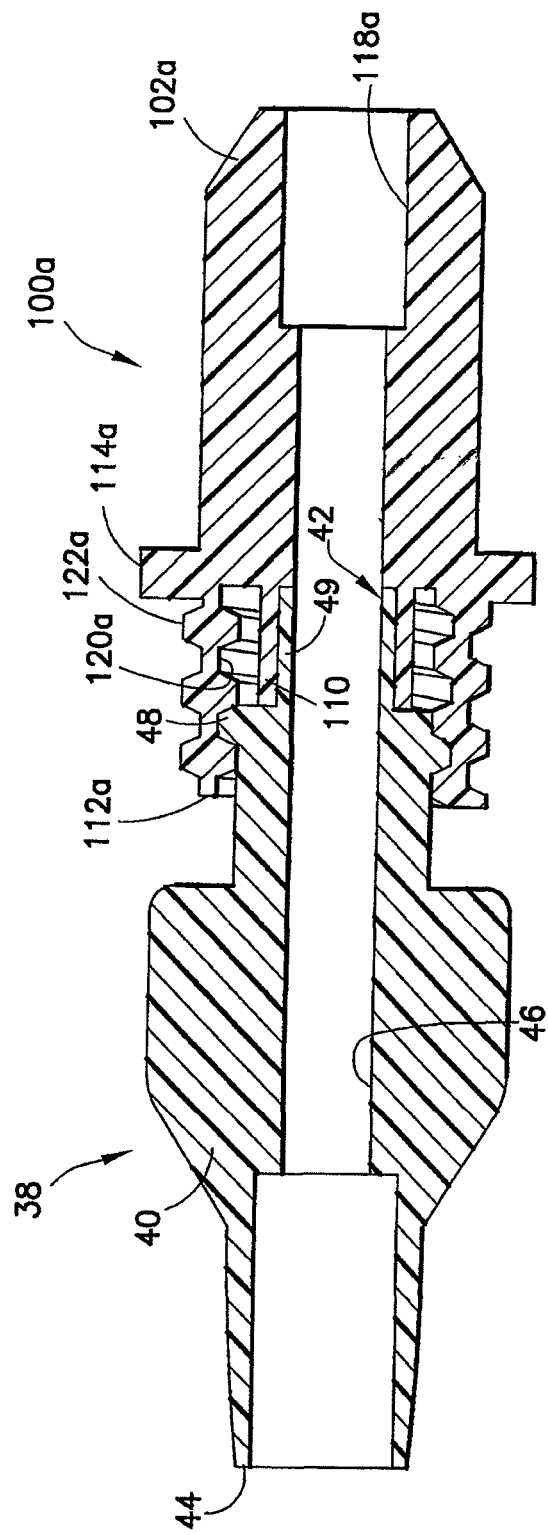
FIG. 13 is a cross-sectional view of an embodiment of the medical connector of FIG. 10 comprising a female luer member, and showing the medical connector engaged with a luer connector with a male luer extension.

Catheter 30 and connector device 5 are joined or connected by inserting male luer member 110 of medical connector 100 into lumen 46 and then threading flange 48 into the internal threads 120 within annular member 112 of medical connector 100. The resulting mating connection between catheter 30 and medical connector 100 and, more particularly, luer connector 38 and medical connector 100 is shown in FIG. 3B. As will be appreciated by those skilled in the art, the choice of providing a "male" luer for luer member 110 in medical connector 100 and a "female" lumen 46 in luer body 40 for accepting male luer member 110 may be reversed, if desired. Accordingly, luer member 110 may be formed as a "female" luer member and luer body 40 may be formed with a "male" luer extension. A possible configuration for this alternative mating configuration is illustrated in FIG. 13, discussed further herein, wherein a male luer extension 49 extends distally from flange 48. As is well known in the medical arts, mating luer member 110 and female lumen 46 may be correspondingly tapered to facilitate insertion of male luer member 110 into female lumen 46, and facilitate frictional engagement therebetween. Such corresponding tapering between mating luer connections is well known in the medical art.

Figure 4A:
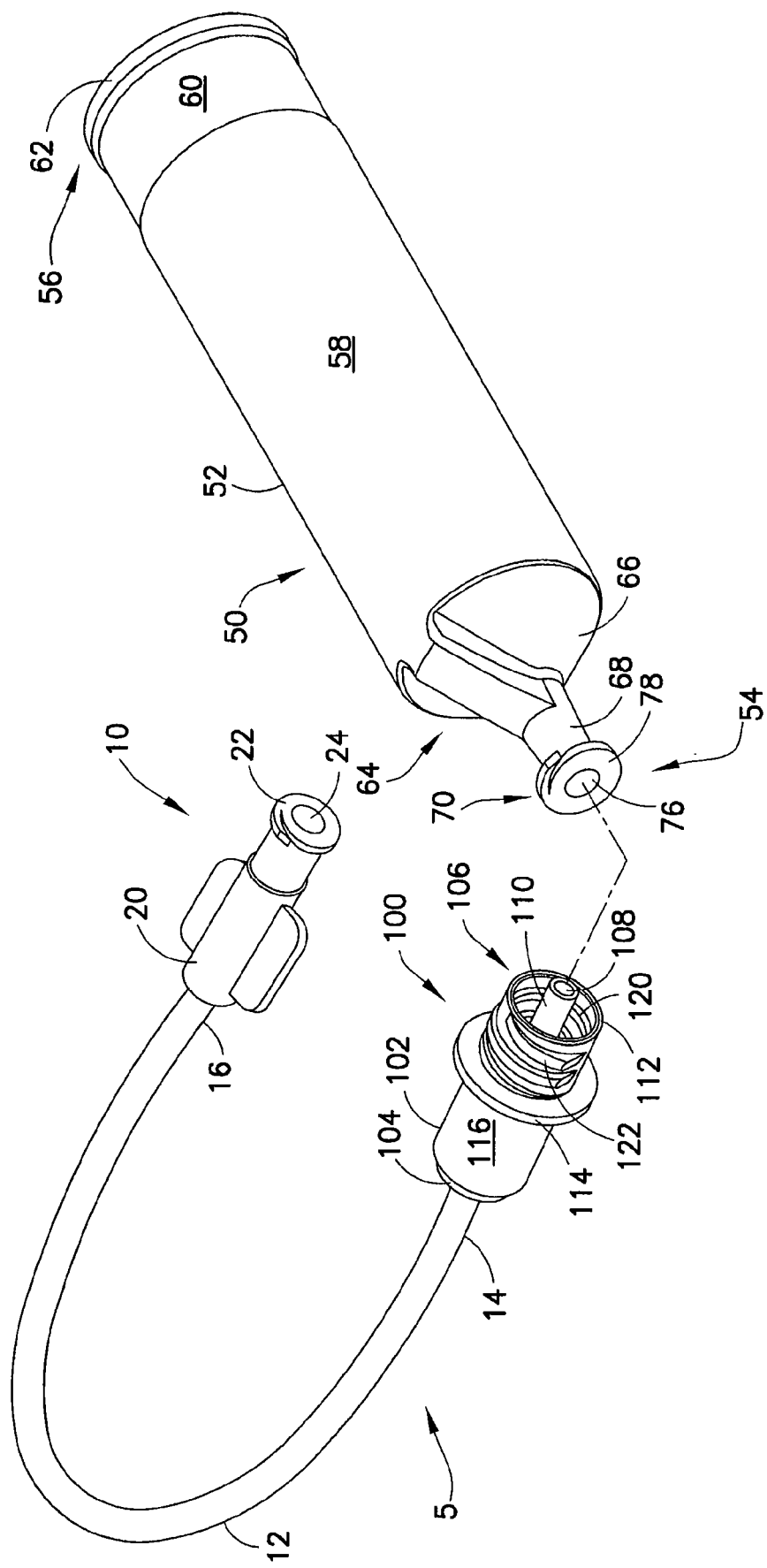
FIG. 4A is a perspective view showing the medical connector of FIG. 1 associated with a syringe having a female luer connector provided on the discharge end of the syringe.
Figure 4B:
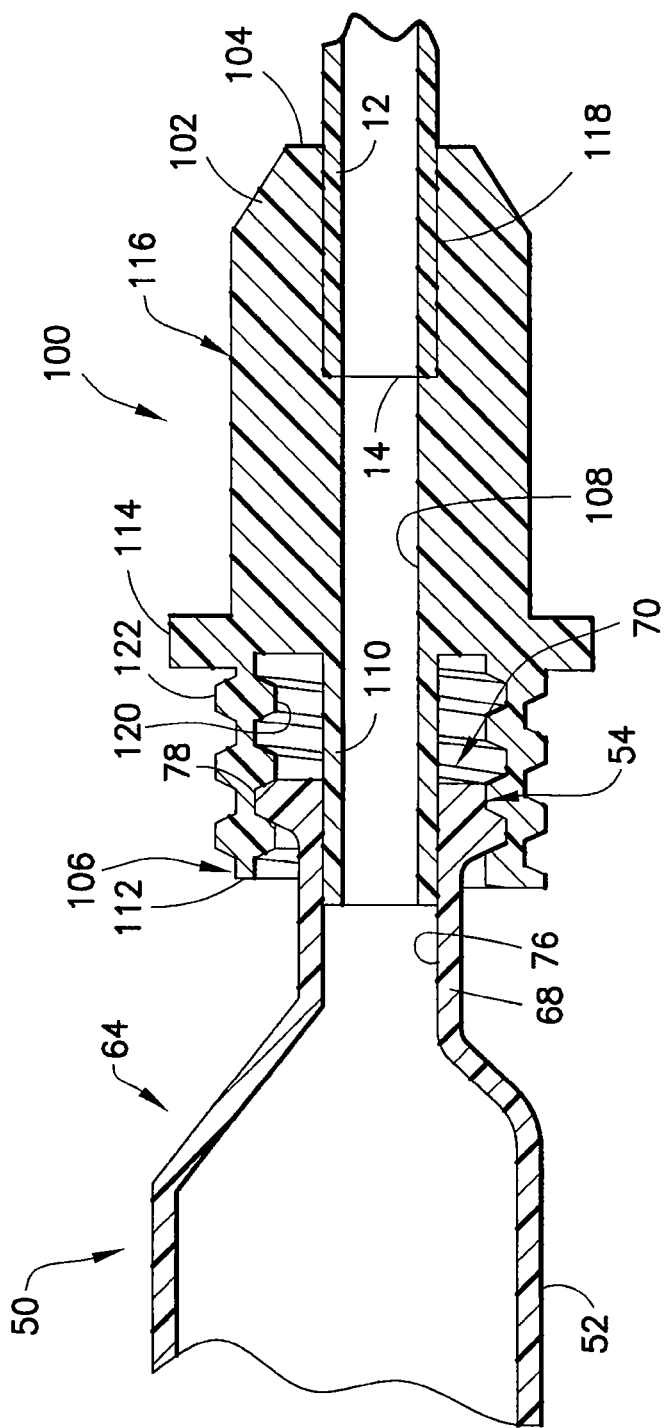
FIG. 4B is a cross-sectional view showing the medical connector of FIG. 1 engaged with the syringe of FIG. 4A.

In FIGS. 4A and 4B, connector device 5 is shown associated with a syringe 50 as another representative mating medical component. The details of syringe 50 are provided in U.S. patent application Ser. No. 10/818,477 (CV/02-014.CIP), filed Apr. 5, 2004 and entitled "Fluid Injection Apparatus with Front Load Pressure Jacket System with Syringe Holder and Light Illumination", assigned to the same assignee as the present application and which is incorporated herein by reference in its entirety. Generally, syringe 50 comprises an elongated, cylindrical syringe body 52 having a front or distal end 54 and a rear or proximal end 56. The syringe body 52 has a main body portion 58 of generally cylindrical shape and uniform diameter, but typically defines an expansion section 60 to accommodate outward expansion of the syringe body 52 in the vicinity of a plunger (not shown) disposed in main body portion 58. A radially-outward extending flange or lip 62 is provided at the proximal end 56 of syringe body 52. An injection section 64 extends distally from main body portion 58, and comprises a conical portion 66 and a discharge outlet 68 extending distally from conical portion 66. Discharge outlet 68 is elongated and has a relatively small inner diameter compared to the inner diameter of main body portion 58. A luer connector 70 is provided at the distal end of discharge outlet 68 for connecting syringe 50 to another medical component. Luer connector 70 is again shown as a standard or conventional female luer connector, much like luer connector 10 and luer connector 38 discussed previously. Luer connector 70 comprises an aperture or opening 76 in fluid communication with discharge outlet 68 and forms the discharge opening from discharge outlet 68. Luer connector 70 further comprises an externally-threaded flange 78 for forming a mating connection with medical connector 100, in a generally similar manner to luer connector 38 discussed previously. Typically, luer connector 70 is formed integrally with the syringe body 52 and discharge outlet 68 in particular.

Syringe 50 and medical connector device 5 are joined or connected by inserting male luer member 110 of medical connector 100 into opening 76 in luer connector 70 and then threading flange 78 of luer connector 70 into internal threads 120 within annular member 112 of medical connector 100. The resulting mating connection between syringe 50 and medical connector 100 and, more particularly, luer connector 70 provided at the distal end 54 of syringe body 52 and medical connector 100 is shown in FIG. 4B. As discussed previously in connection with FIGS. 3A and 3B, the choice of providing a "male" luer for luer member 110 in medical connector 100 and a "female" opening or aperture 76 in luer connector 70 for accepting male luer member 110 may be reversed, if desired.

Figure 5:
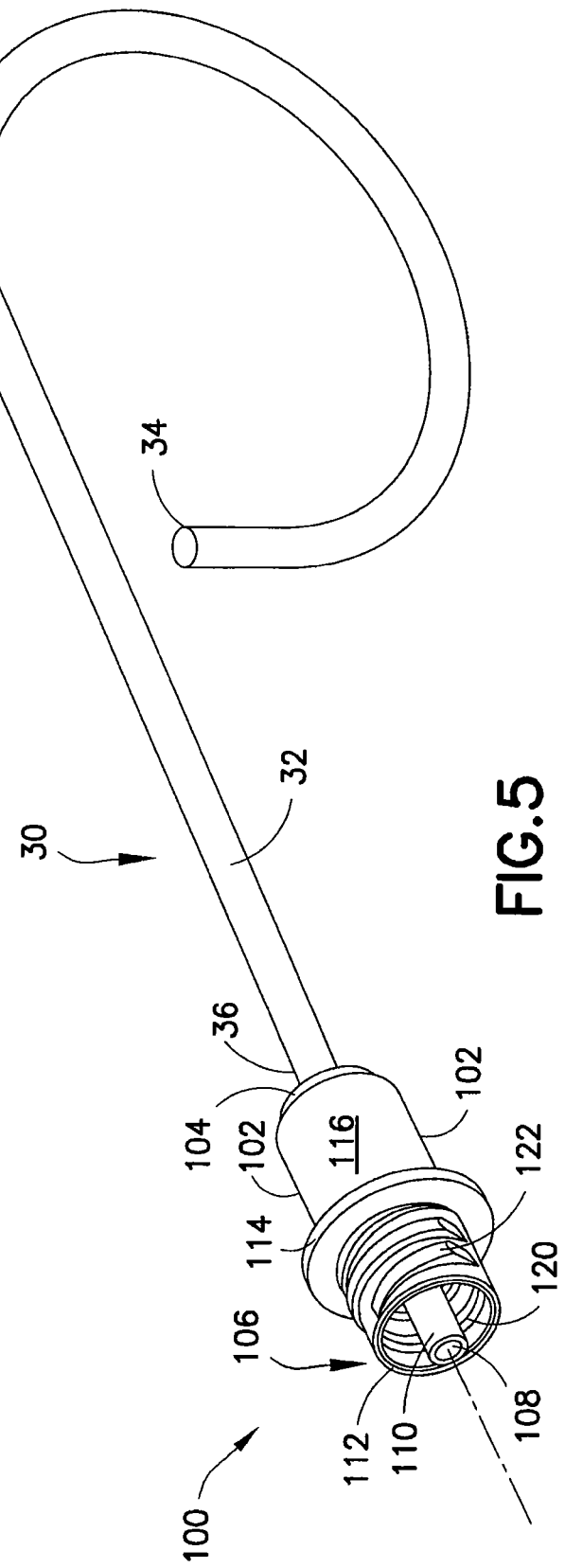
FIG. 5 is a perspective view of a catheter comprising the medical connector of FIG. 1 provided on a proximal end of the catheter in accordance with a further aspect of the invention.
Figure 6:
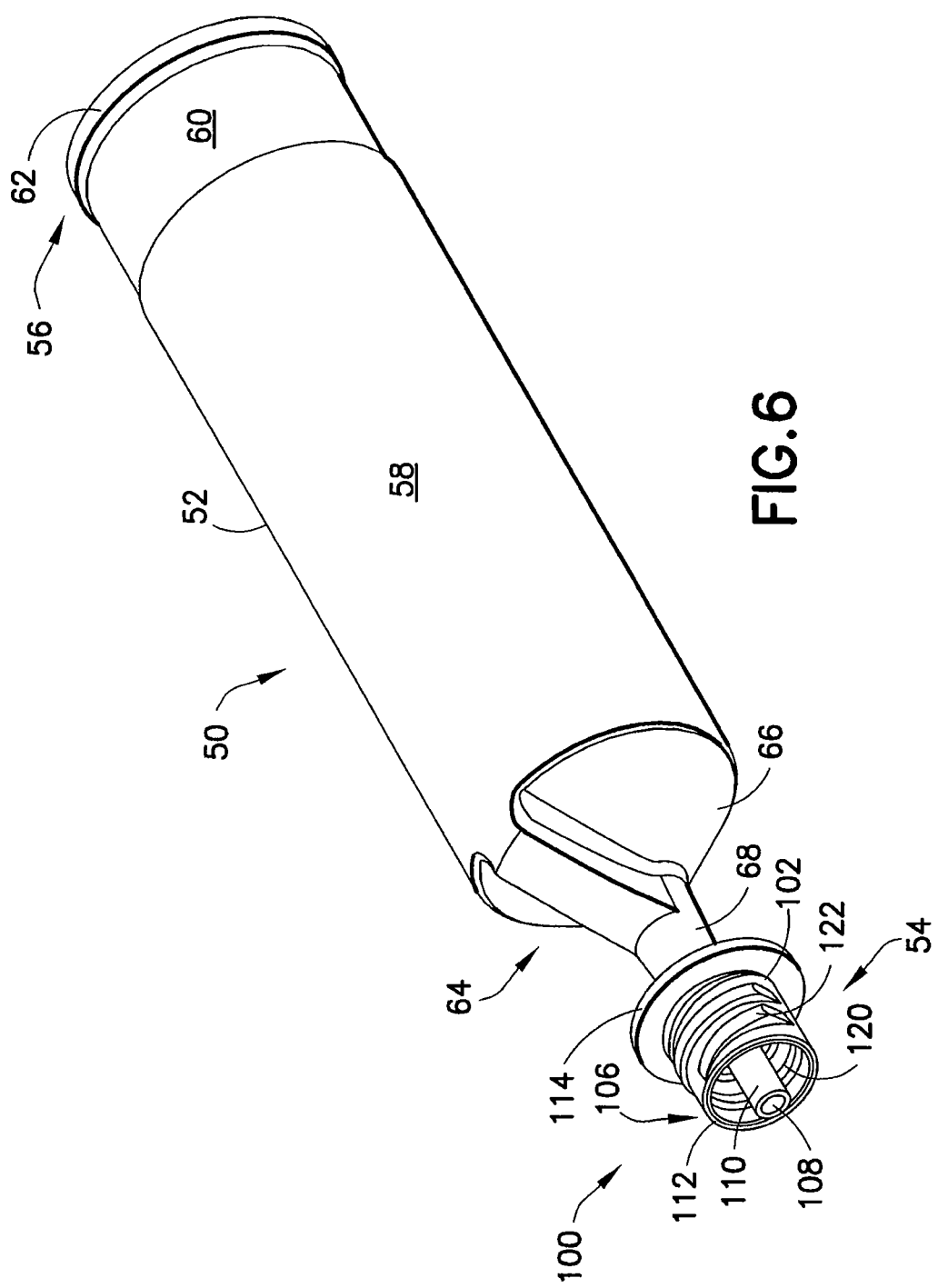
FIG. 6 is a perspective view of a syringe comprising the medical connector of FIG. 1 disposed on the discharge end of the syringe in accordance with another aspect of the invention.

FIGS. 5 and 6 illustrate other aspects of the invention, wherein catheter 30 and syringe 50 each include medical connector 100 provided in place of "standard" or "conventional" luer connectors 38, 70, respectively. In FIG. 5, medical connector 100 is provided in place of luer connector 70 at the proximal end 36 of catheter body 32 of catheter 30. Similarly, as shown in FIG. 6, medical connector 100 is provided in place of luer connector 70 at the distal end of discharge outlet 68 of syringe body 52 of syringe 50. In catheter 30 and syringe 50, medical connector 100 may comprise either a "male" luer member 110 or a "female" luer member 110 as discussed previously in connection with FIGS. 3A-3B and 4A-4B. Accordingly, both catheter 30 and syringe 50 may be adapted to connect with a standard or conventional externally-threaded "female" luer connector such as luer connectors 38, 70 discussed previously, or even luer connector 10 of connector device 5. Additionally, as discussed previously, due to the additional presence of external engagement structure or external threads 122 on annular member 112, medical connector 100 associated with catheter 30 and syringe 50 is suitable for engaging an internally-threaded mating medical component, such as mating medical connector 200 discussed herein or even another medical connector 100 with a suitably sized (e.g., enlarged) annular member 112, and appropriately configured luer member 110. Medical connector 100 may be formed integrally with the catheter body 32 of catheter 30 and the syringe body 52 of syringe 50 in, for example, a plastic molding process, but may also be provided as a separate element that is secured to the proximal end 36 of catheter body 32 and discharge outlet 68 of syringe body 52 by conventional means in the medical field (i.e., adhesive, welding, etc.). Similar techniques may be used to fix medical connector 100 to tubing 12 discussed previously in connection with FIGS. 1-2.

Figure 7B:
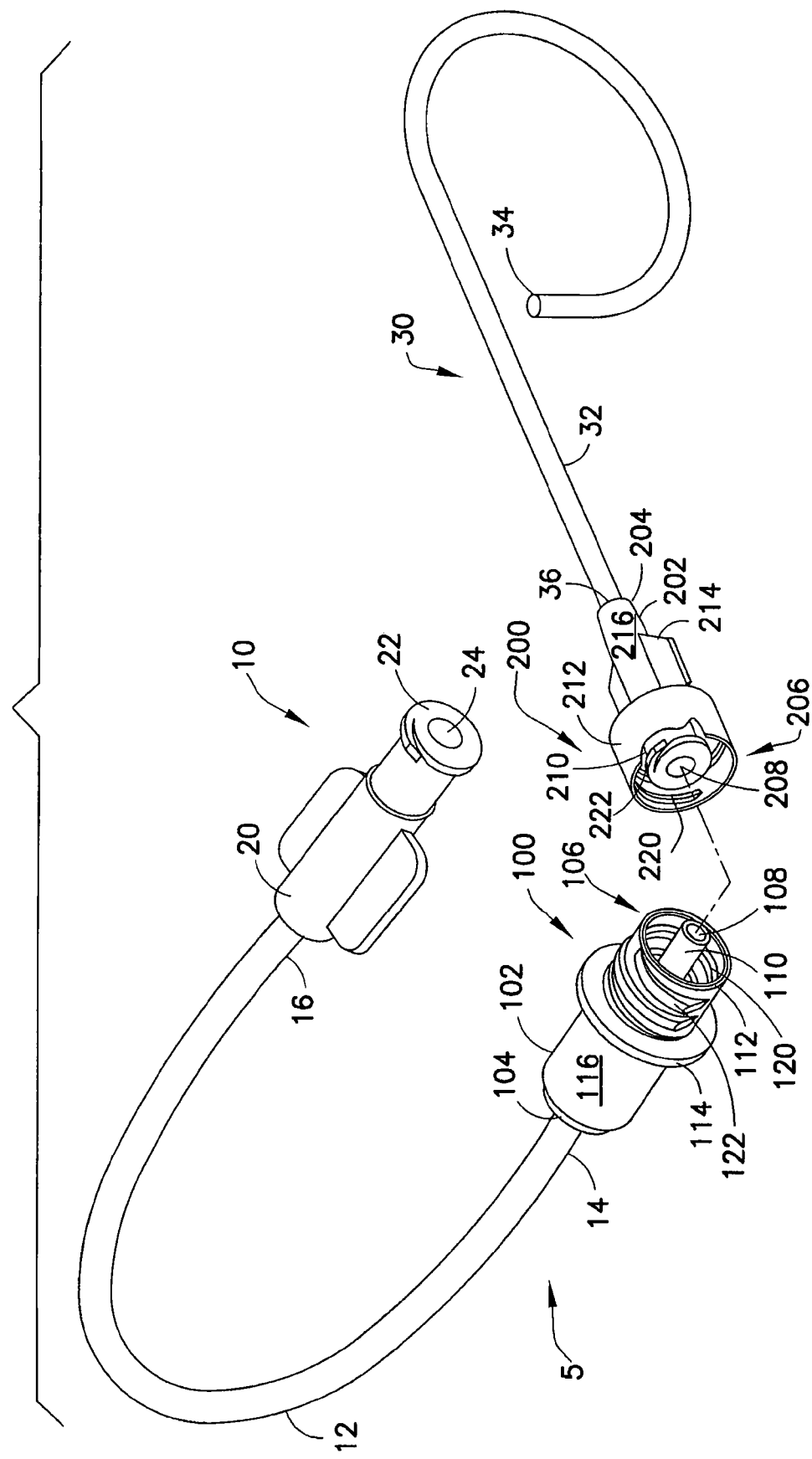
FIG. 7B is a perspective view showing the medical connector device of FIG. 1 associated with the catheter of FIG. 7A, wherein the mating medical connector further comprises a luer member adapted to engage the medical connector of FIG. 1.

Referring to FIGS. 7A-7B, catheter 30, discussed previously, is shown with a medical connector 200 according to another aspect of the present invention provided in place of standard or conventional female luer connector 38. While medical connector 200 is shown associated with catheter 30, medical connector 200 may also be provided in place of medical connector 100 in connector device 5, if desired. Additionally, as discussed herein in connection with FIGS. 8A-8B, medical connector 200 may be provided in place of luer connector 70 at the distal end of discharge outlet 68 of syringe body 52 of syringe 50. In FIGS. 7A-7B, medical connector 200 is connected to the proximal end 36 of catheter body 32 in a generally similar manner to luer connector 38 and is used to form a mating connection with another medical component such as connector device 5 and medical connector 100 thereof. Medical connector 200 is connected to catheter body 32 typically in the same manner as luer connector 38, for example, by a suitable medical grade adhesive or by being formed integrally with catheter body 32, as discussed further herein in connection with FIGS. 9A-9C.

Medical connector 200 is generally adapted as a mating component or connector to medical connector 100, and medical connectors 100, 200 may be referred to as "first" and "second" connectors 100, 200, respectively, in this disclosure. Medical connector 200 generally comprises a unitary body 202 having a first or proximal end 204 and a second or distal end 206. Connector body 202 defines a lumen 208 for fluid flow through medical connector 200. Connector body 202 is further formed with a luer member 210 which extends distally from the connector body 202 and which, at least in part, defines or forms lumen 208. Luer member 210 is illustrated as a "female" luer member for receiving the "male" luer member 110 of medical connector 100, but may also be formed as a male luer member, as shown in FIG. 9B discussed herein, for engaging a female luer member 110 of medical connector 100. Connector body 202 is further formed with an annular member 212 disposed about luer member 210. Annular member 212 may be coaxially disposed about luer member 210, and luer member 210 is typically recessed within annular member 212 in the embodiment of medical connector 200 shown in FIGS. 7A-7B and 8A-8B, but may also project distally outward from annular member 212, if necessary, in the same manner as luer member 110 of medical connector 100 discussed previously, if desired. This alternative configuration of luer member 210 and annular member 212 may useful for completing a mating connection with medical connector 100a discussed herein in connection with FIG. 10, wherein a recessed luer member 100a is provided within annular member 112a.

Connector body 202 may further be formed with wings 214 extending outward from connector body 202 to provide surfaces for the user of medical connector 200 to grasp when connecting medical connector 200 to medical connector 100 or another mating medical component, such as catheter 30 and syringe 50 of FIGS. 5 and 6 discussed previously. When the user of medical connector 200 is ready to connect the medical connector 200 to another component, the user typically grasps wings 214 between his or her thumb and index finger which allow the user to hold the medical connector 200 steady while a mating medical component, such as medical connector 100, is threaded into engagement with medical connector 200. An outer surface 216 of connector body 202 may also be grasped by the user to hold medical connector 200 steady during the connecting process. If desired, annular member 212 may be rotationally connected to connector body 202 in a similar manner to the way annular member 112 is connected to connector body 102 in FIG. 2A, to allow rotation of annular member 212 relative to connector body 202 in medical connector 200.

Figure 9A:
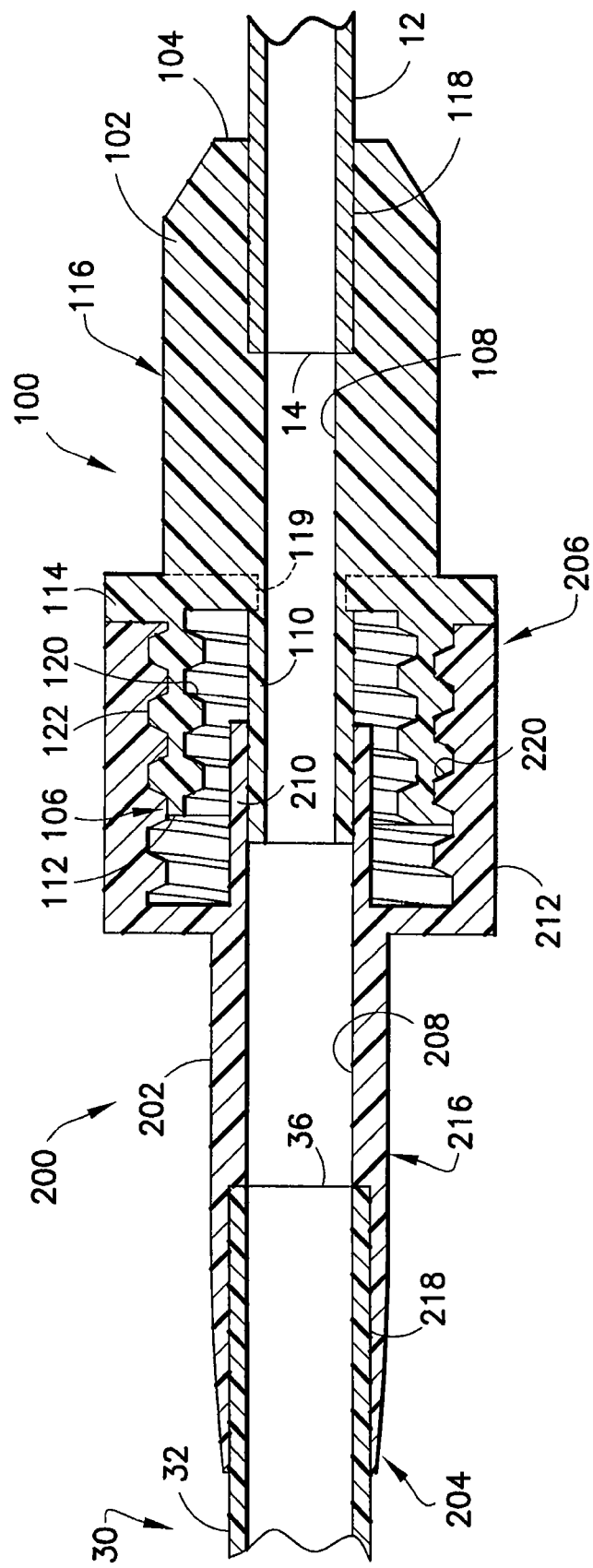
FIG. 9A is a cross-sectional view showing the medical connector of FIG. 1 engaged with the mating medical connector associated with the catheter of FIG. 7A and syringe of FIG. 8A.
Figure 9B:
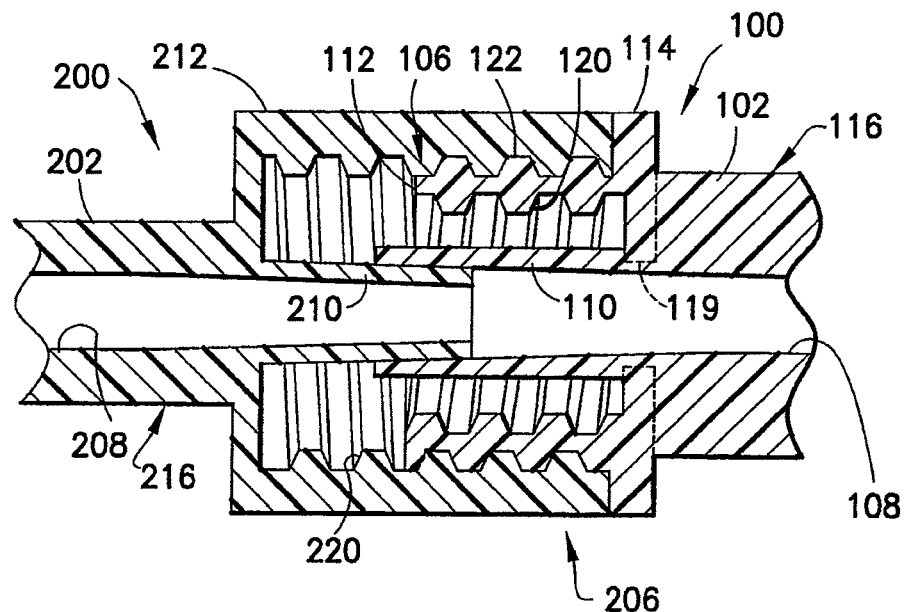
FIG. 9B is a cross-sectional view of an embodiment of the medical connector of FIG. 1 comprising a female luer member, and showing the medical connector of FIG. 1 engaged with an embodiment of the mating medical connector shown in FIGS. 7A and 8A comprising a male luer member.
Figure 10:
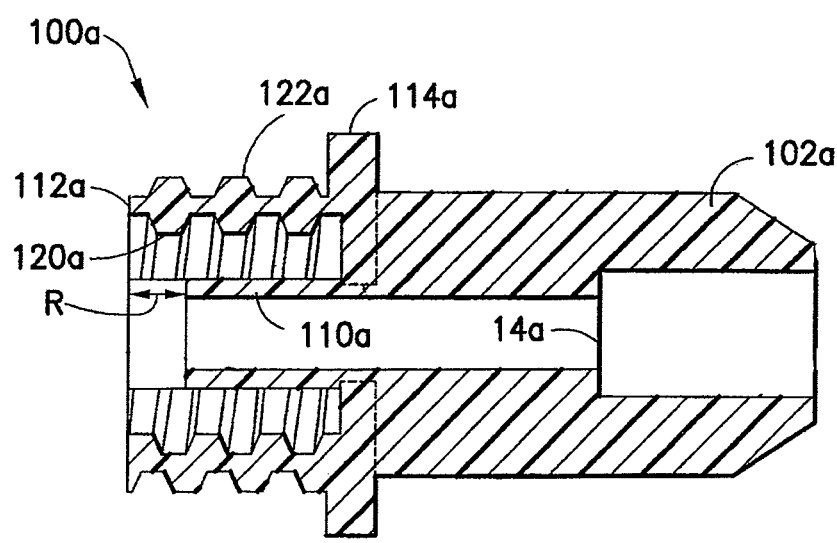
FIG. 10 is a cross-sectional view of another embodiment of the medical connector of FIG. 1 comprising a recessed luer member.
Figure 9C:
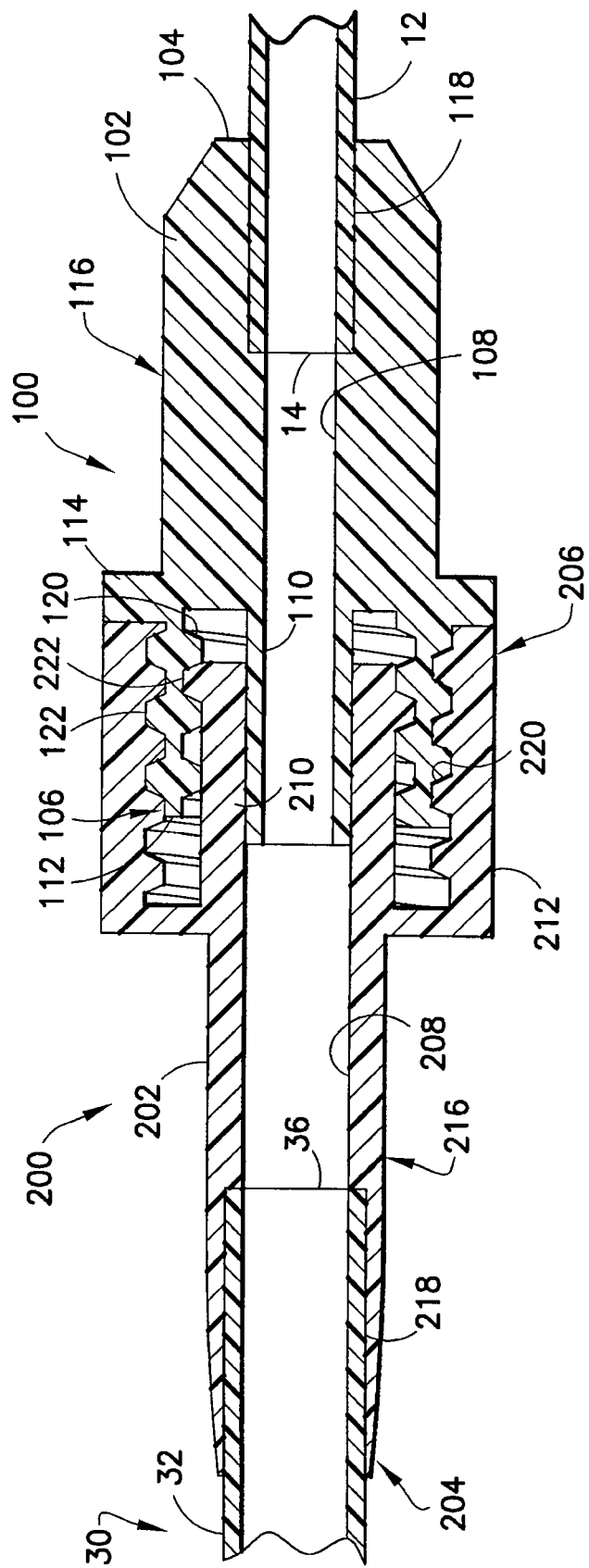
FIG. 9C is a cross-sectional view showing the medical connector of FIG. 1 engaged with the mating medical connector shown associated with the catheter of FIG. 7B and syringe of FIG. 8B.

Lumen 208, as shown in FIGS. 9A-9C discussed herein, defines a recessed area 218 for accepting the proximal end 36 of catheter body 32 or, alternatively, medical tubing such as tubing 12 of connector device 5, should it be desired to include medical connector 200 in place of medical connector 100 in connector device 5. The proximal end 36 of catheter body 32 (or the first end 14 of tubing 12) is typically adhesively secured within recessed area 218 by a suitable medical grade adhesive. Typically, annular member 212 of connector body 202 is sized (e.g., enlarged) sufficiently to accept or receive annular member 112 of medical connector 100, as discussed herein in connection with FIGS. 9A-9C, to allow engagement between annular member 212 and annular member 112. Accordingly, annular member 212 of medical connector 200 is formed with internal engagement structure 220, typically internal threads as illustrated, for engaging the internal threads 120 within the annular member 112 of medical connector 100 to secure the connection between medical connectors 100, 200. Additionally, the internal engagement structure (hereinafter "internal threads") 220 within annular member 212 of medical connector 200 may be used to form a connecting engagement with an eternally-threaded connector element or component such as luer connectors 38, 70 associated with catheter 30 and syringe 50 discussed previously in connection with FIGS. 3A-3B and 4A-4B, provided luer member 210 is configured as a male luer member.

In general, the connection between catheter 30 and connector device 5 in FIG. 7A is accomplished by inserting male luer member 110 of medical connector 100 into female luer member 210 of mating medical connector 200, and then threading annular member 112 of medical connector 100 into engagement within annular member 212 so that a threaded engagement is established between the external threads 120 on annular member 112 and the internal threads 220 within in annular member 212. As described previously, the choice of providing a "male" luer for luer member 110 in medical connector 100 and a "female" luer for luer member 210 in medical connector 200 may be reversed, if desired. Accordingly, luer member 110 may be formed as a female luer member and female luer member 210 may be formed as a male luer member. This alternative mating configuration is illustrated in FIG. 9B, discussed further herein. Again, as described previously, mating luer members 110, 210 may be correspondingly tapered to facilitate insertion of male luer member 110 into female luer member 210 (and vice versa). Such corresponding tapering between mating luer connections is well known in the medical art.

In a further and preferred extension of medical connector 200 shown in FIG. 7B, luer member 210 may be formed with an externally-threaded flange 222, generally similar to flanges 48, 78 of luer connectors 38, 70 associated with catheter 30 and syringe 50 discussed previously in connection with FIGS. 3A-3B and 4A-4B. Accordingly, threaded flange 222 is typically &tined integrally with luer member 210 at the distal end thereof and, in combination with internal threads 220 within annular member 212 allows a "double-threaded" connection to be established between mating medical connectors 100, 200. For example, when catheter 30 and connector device 5 shown in FIG. 7B are connected, threaded flange 222 at the distal end of luer member 210 is threaded into engagement with internal threads 120 within annular member 112 of medical connector 100 of connector device 5 while, simultaneously, annular member 112 is threaded into engagement within annular member 212 of medical connector 200. The external threads 122 on annular member 112 of medical connector 100 engages the internal threads 220 within annular member 212 of medical connector 200 to complete the "double-threaded" engagement. The mating thread pitch for the threaded connection between external threads 122 and internal threads 220 and the mating thread pitch between the threaded flange 222 and the internal threads 120 may defined so that both threaded connections may be made simultaneously.

Figure 8A:
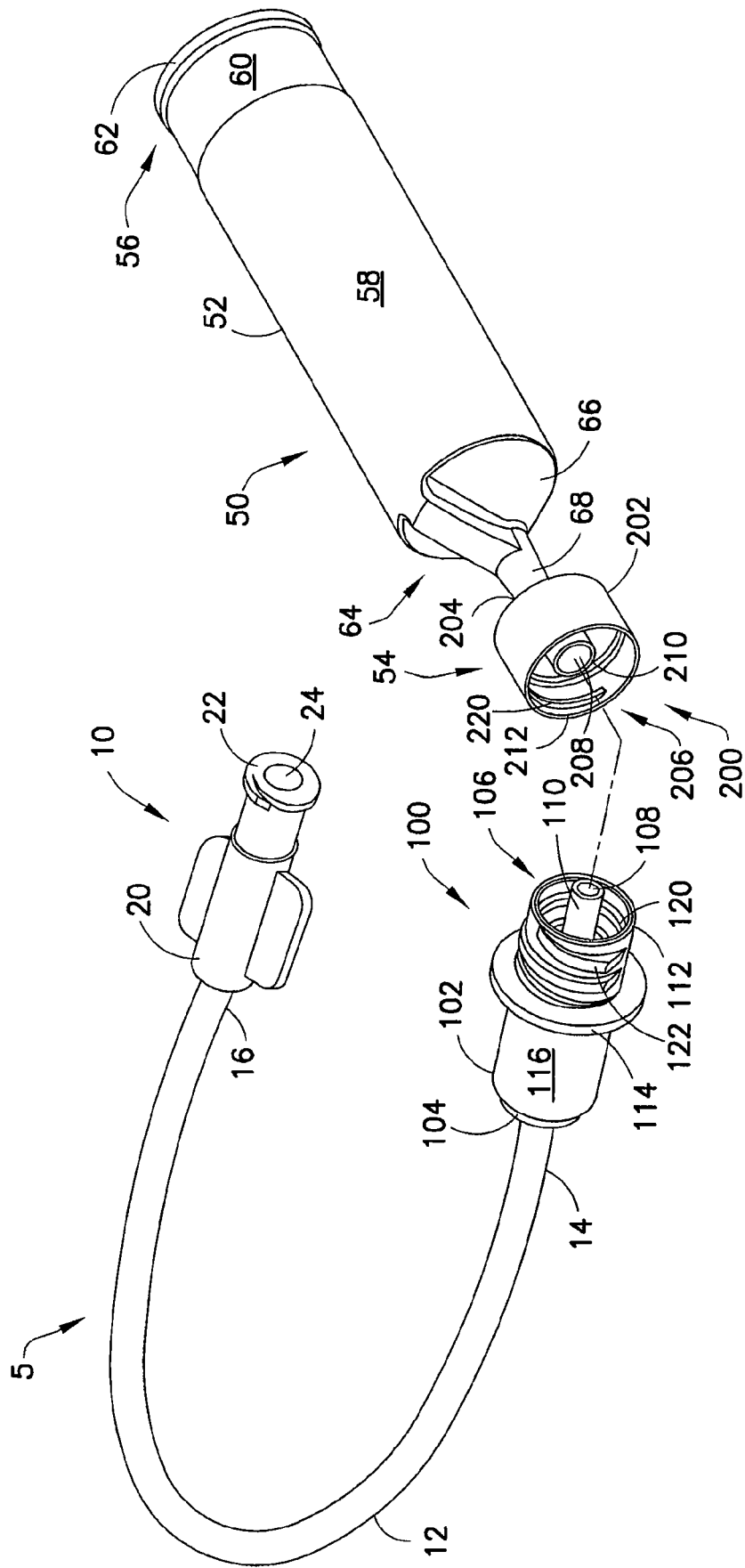
FIG. 8A is a perspective view showing the medical connector device of FIG. 1 associated with a syringe comprising the mating medical connector of FIG. 7A provided on the discharge end of the syringe.
Figure 8B:
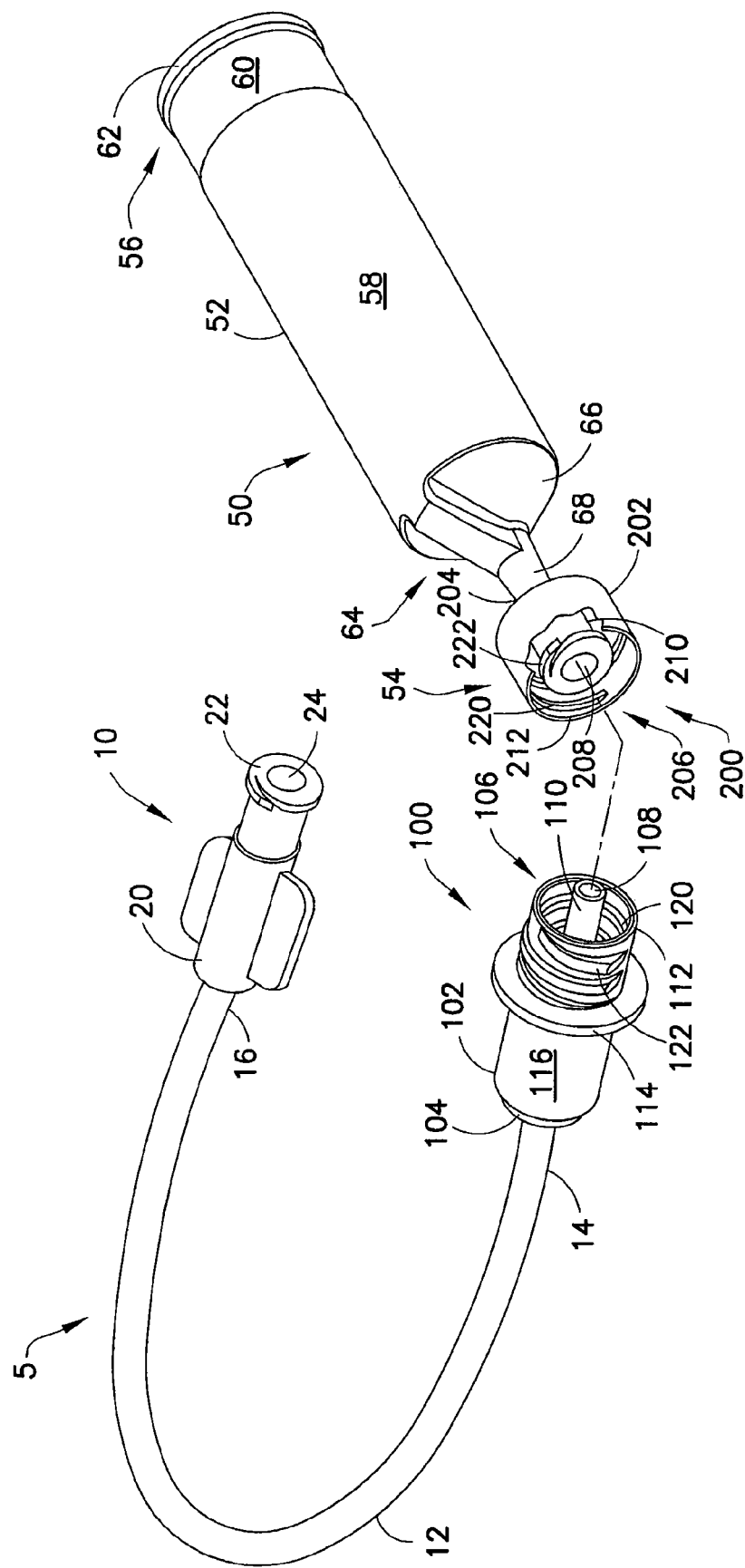
FIG. 8B is a perspective view showing the medical connector device of FIG. 1 associated with the syringe of FIG. 8A, with the mating medical connector further comprising a luer member adapted to engage the medical connector of FIG. 1.

Referring to FIGS. 8A-8B, as indicated previously, medical connector 200 may also be associated with syringe 50. In FIGS. 8A-8B, medical connector 200 is provided in place of luer connector 70 at the end of discharge outlet 68 of syringe body 52. Thus, medical connector 200 may be provided at the distal end 54 of syringe body 52 of syringe 50, for connecting syringe 50 to another medical component, such as mating medical connector 100 in connector device 5. In FIG. 8A, medical connector 200 is formed in an analogous manner to medical connector 200 depicted in FIG. 7A associated with catheter 30, and comprises a female luer member 210 coaxially disposed within annular member 212. Similarly, medical connector 200 shown in FIG. 8B further comprises threaded flange 222 provided at the distal end of luer member 210 in generally the same manner as the medical connector 200 shown in FIG. 7B. Accordingly, syringe 50 comprising medical connector 200 connects with medical connector 100 of, for example, connector device 5 in the same manner as discussed previously with the catheter 30 of FIGS. 7A-7B. Once again, the male luer configuration of luer member 110 in medical connector 100 and female luer configuration of luer member 210 in medical connector 200 may be reversed in the embodiment of syringe 50 shown in FIG. 8A, if desired. Likewise, medical connector 200 of FIG. 8B is adapted to form a "double-threaded" connection with medical connector 100 in the manner described previously.

FIGS. 9A-9C are cross-sectional views showing the connection between mating medical connectors 100, 200 of, in particular, FIGS. 7A and 7B, but are also illustrative of the mating connections between medical connectors 100, 200 in FIGS. 8A and 8B. In FIG. 9A, as described previously, the male luer member 110 of medical connector 100 is received into corresponding female luer member 210 of mating medical connector 200 connected to catheter 30. Additionally, annular member 112 of medical connector 100 forms a threaded engagement with annular member 210 of medical connector 200, with external threads 122 on annular member 120 engaged with internal threads 220 in annular member 212. FIG. 9B illustrates the reverse luer connection for luer members 110, 210 from that shown in FIG. 9A. Accordingly, in FIG. 9B, luer member 110 of medical connector 100 is now formed as a female luer member 110 which receives male luer member 210 of medical connector 200. Finally, FIG. 9C shows the "double-threaded" engagement between medical connectors 100, 200 provided by the addition of threaded flange 222 on luer member 210 of medical connector 200. In FIG. 9C, as described previously, threaded flange 222 at the distal end of luer member 210 is threaded into engagement with internal threads 120 within annular member 112 of medical connector 100 while, simultaneously, the external threads 122 on annular member 112 of medical connector 100 are threaded into engagement with the internal threads 220 within annular member 212 of medical connector 200, to form the "double-threaded" connection. As illustrated in dashed lines in FIGS. 9A-9C, circumferential flange 114 and annular member 112 of medical connector 100 may be adapted for rotation relative to connector body 102 to facilitate the threaded engagement of the "male" medical connector 100 into "female" medical connector 200. While not illustrated in FIGS. 9A-9C, annular member 212 of medical connector 200 may also be provided as a rotational element on connector body 202, in a similar manner to circumferential flange 114 and annular member 112 of medical connector 100. In this optional variation of medical connector 200, circumferential flange 114 and annular member 112 are preferably formed integral with connector body 102 as shown in FIG. 2 and thus not rotationally connected to connector body 102.

Figure 11A:
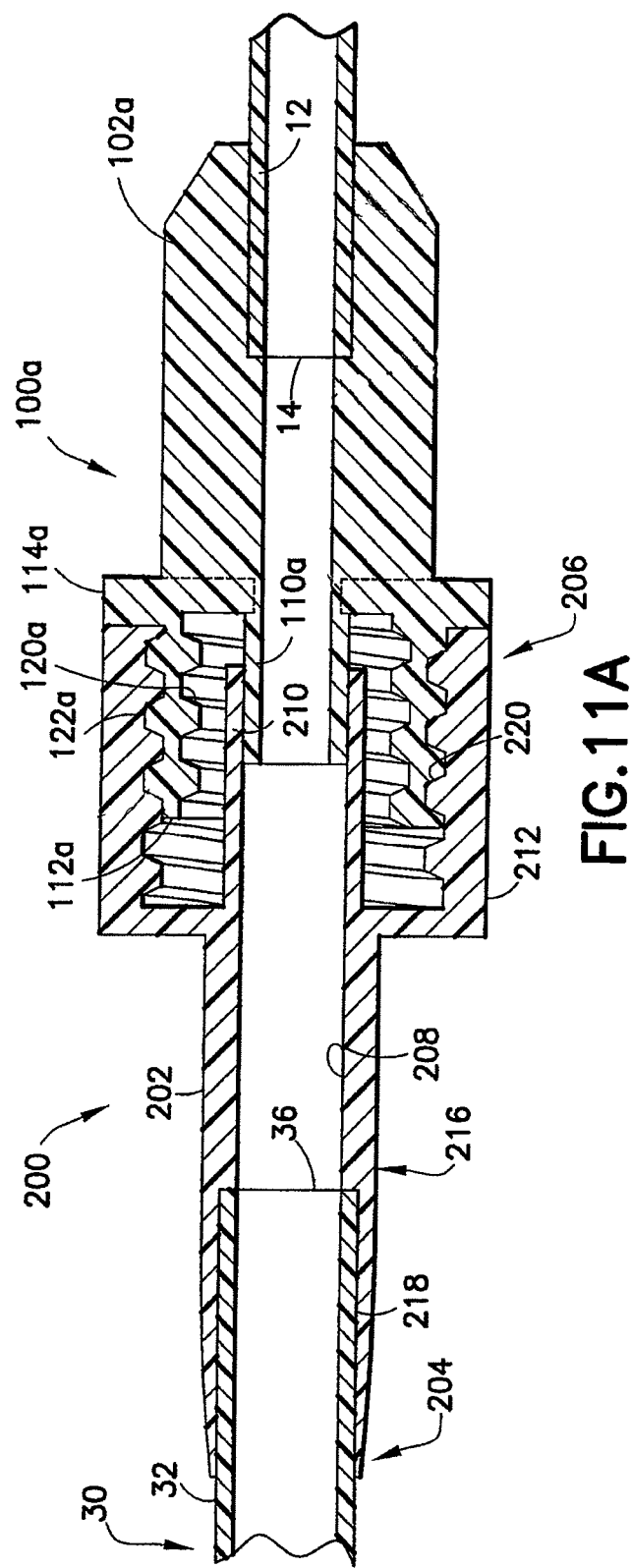
FIG. 11A is a cross-sectional view showing the medical connector of FIG. 10 engaged with the mating medical connector associated with the catheter of FIG. 7A and syringe of FIG. 8A.
Figure 11B:
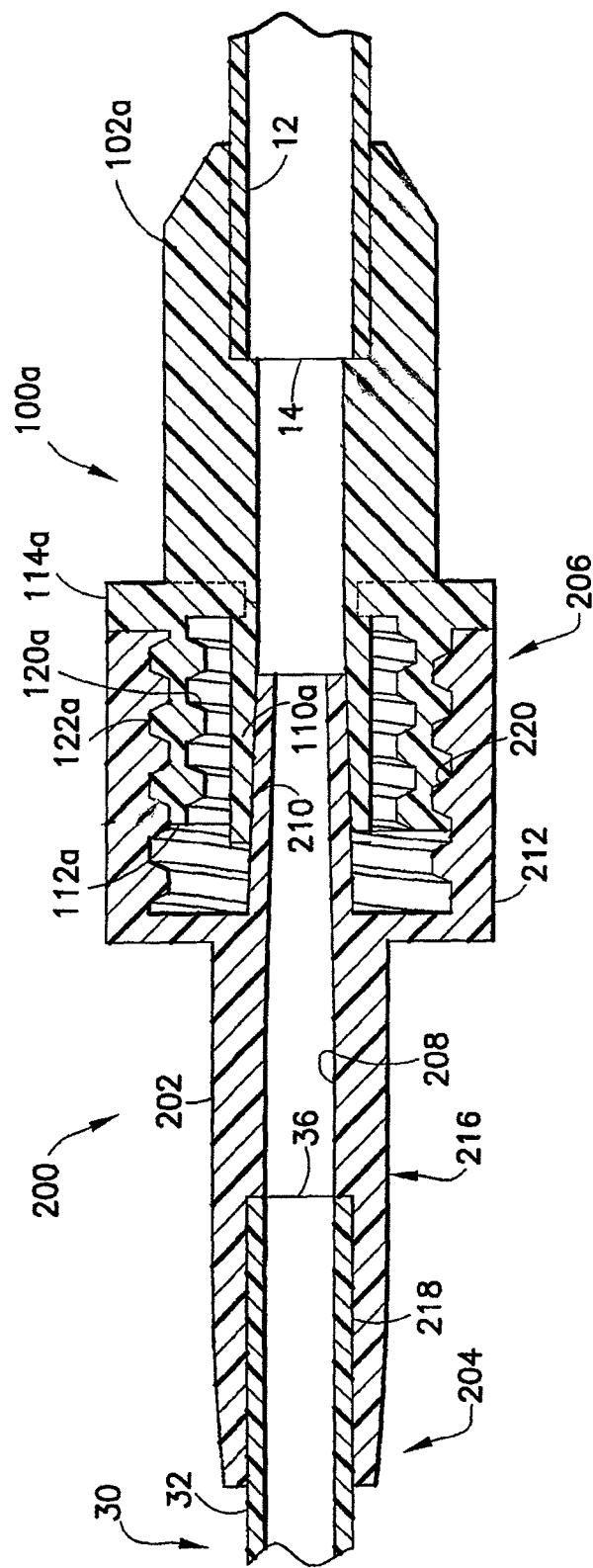
FIG. 11B is a cross-sectional view of an embodiment of the medical connector of FIG. 10 comprising a female luer member, and showing the medical connector engaged with an embodiment of the mating medical connector shown in FIGS. 7A and 8A comprising a male luer member.
Figure 11C:
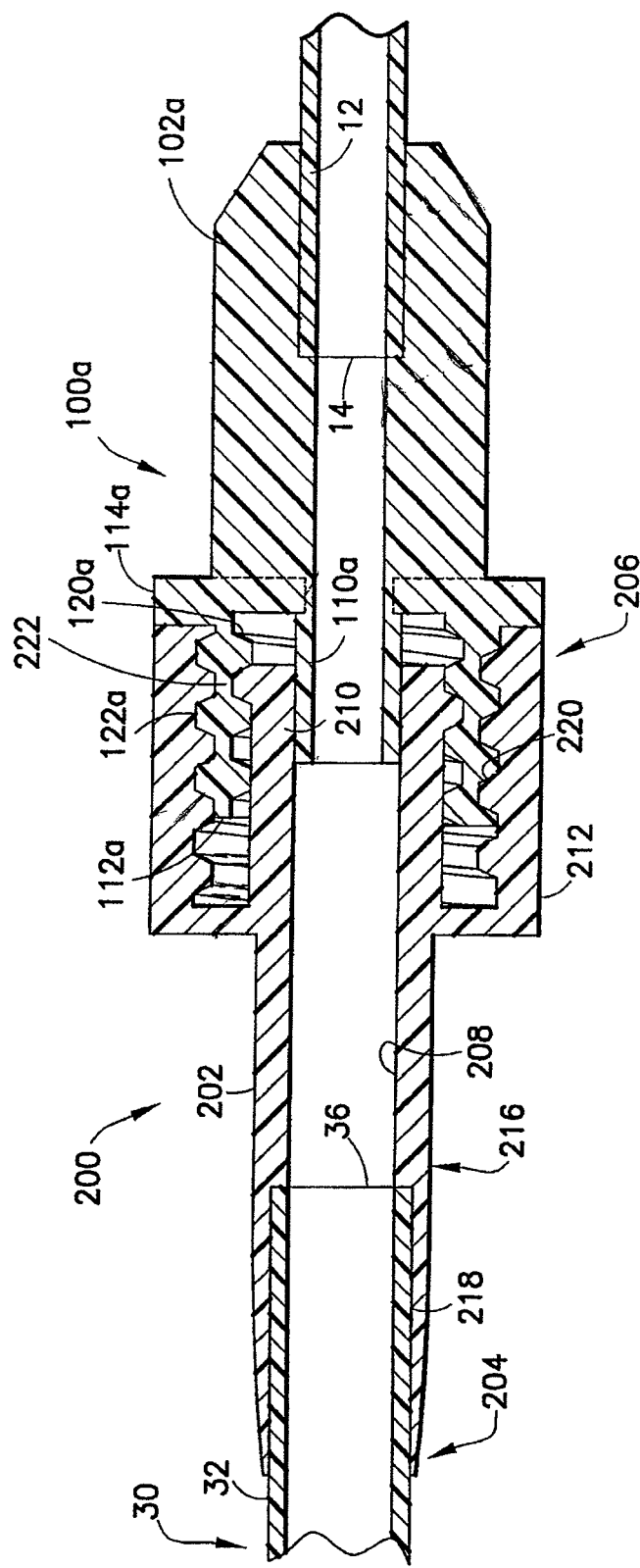
FIG. 11C is a cross-sectional view showing the medical connector of FIG. 10 engaged with the mating medical connector associated with the catheter of FIG. 7B and syringe of FIG. 8B.
Figure 12A:
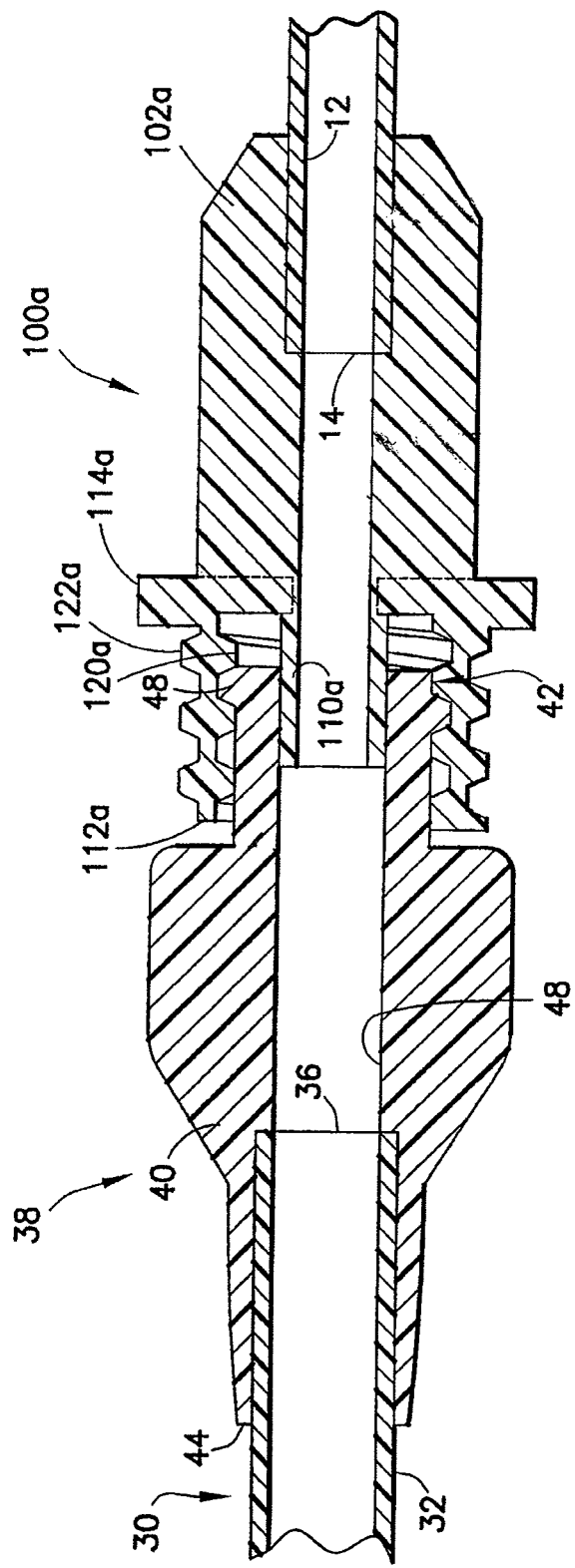
FIG. 12A is a cross-sectional view showing the medical connector of FIG. 10 engaged with the catheter of FIG. 3A.
Figure 12B:
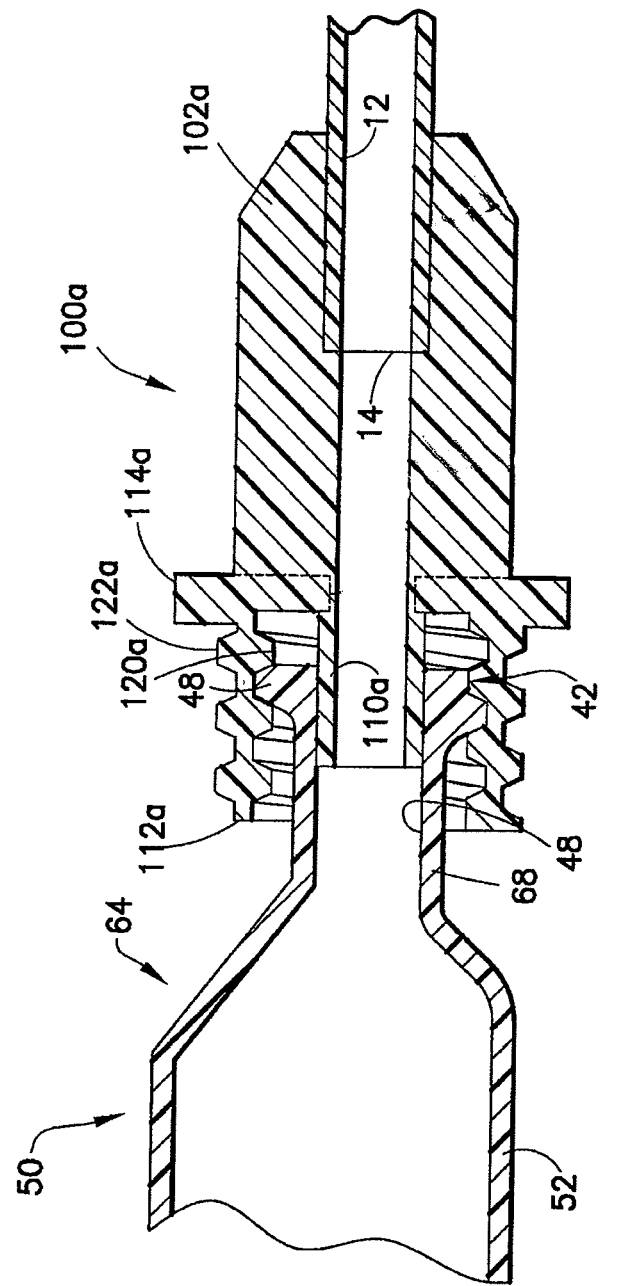
FIG. 12B is a cross-sectional view showing the medical connector of FIG. 10 engaged with the syringe of FIG. 4A.

Referring to FIGS. 10-12, another embodiment of medical connector 100a is shown associated with catheter 30 described previously. Medical connector 100a is identical in all respects to medical connector 100 discussed previously in detail in connection with FIGS. 1 and 2, but comprises a recessed luer member 110a. More particularly, connector body 102a is formed with luer member 110a disposed axially inward from annular member 112a, thereby locating the tip of luer member 110a within annular member 112a. Accordingly, luer member 110a is recessed a distance R from the distal opening formed or defined by annular member 112a, which prevents inadvertent contact with luer member 110a and improving the sterility of medical connector 100a.

FIGS. 11A-11C are cross-sectional views showing the connection between mating medical connectors 100a, 200, with medical connector 100a illustrated as forming part of connector device 5 and mating medical connector 200 illustrated as forming the connecting portion of catheter 30. Medical connector 200 is generally similar medical connector 200 illustrated in FIGS. 7A-7B and 8A-8B. Medical connector 200 described previously in connection with these Figures comprises a luer member 210 generally recessed within annular member 212 of connector body 202. However, as medical connector 200 is now associated with medical connector 100a comprising a generally recessed luer member 110a, it may be desirable to extend the length of luer member 210 in medical connector 200 so that sufficient engagement occurs between luer members 110, 210 of medical connectors 100, 200. The optional "extended" length of luer member 210 in the medical connector 200 of FIGS. 11A-11C is apparent when comparing these Figures to FIGS. 9A-9C discussed previously. While luer member 210 is still shown slightly recessed within annular member 212 in FIGS. 11A-11C, luer member 210 may optionally extend or project outward from annular member 212 if desired.

In FIG. 11A, as in FIG. 9A described previously, male luer member 110a of medical connector 100a is received into corresponding female luer member 210 of mating medical connector 200 connected to catheter 30. Additionally, annular member 112a of medical connector 100a forms a threaded engagement with annular member 210 of medical connector 200, with external threads 122a on annular member 120a engaged with internal threads 220 in annular member 212. FIG. 11B illustrates the reverse luer connection for luer members 110a, 210 from that shown in FIG. 11A. Further, FIG. 11C shows the "double-threaded" engagement between medical connectors 100a, 200 provided by the addition of threaded flange 222 on luer member 210 of medical connector 200. In FIG. 11C, threaded flange 222 at the distal end of luer member 210 is threaded into engagement with internal threads 120a within annular member 112 of medical connector 100a while, simultaneously, the external threads 122a on annular member 112a of medical connector 100a are threaded into engagement with the internal threads 220 within annular member 212 of medical connector 200, to form the "double-threaded" connection. As illustrated in dashed lines in FIGS. 11A-11C, circumferential flange 114a and annular member 112a of medical connector 100 may be adapted for rotation relative to connector body 102a. Moreover, as described in connection FIGS. 11A-11C, annular member 212 of medical connector 200 may also be provided as a rotational element on connector body 202.

FIG. 13 illustrates "recessed" medical connector 100a connected to luer connector 38 described previously in connection with FIGS. 3A-3B, but further comprising male luer extension 49 extending distally from flange 48. Luer connector 70 described previously is generally analogous to luer connector 38 but associated with syringe 50 rather than catheter 30, and may also comprise a similar male luer extension 49 extending from flange 78. Medical connector 100a shown in FIG. 13 comprises a "female" luer member 110a in a similar manner to medical connector 100a of FIG. 11B, discussed previously. Thus, medical connector 100a may be adapted to cooperate with an externally-threaded luer connector such as luer connector 38 comprising a projecting male luer extension 49. To connect luer connector 38 to medical connector 100a, flange 48 of luer connector 38 is threaded into annular member 112a of medical connector 100a until male luer extension 49 of luer connector 38 is received into female luer member 110a of medical connector 100a thereby allow fluid communication between medical connector 100a and luer connector 38. The threaded connection between flange 48 and annular member 112a is generally analogous to the connection between flange 48 and annular member 112 shown in FIG. 3B. However, due to the shortened or recessed form of luer member 110a, flange 48 may need to be further threaded into annular member 112a to ensure that male luer extension 49 is received sufficiently into female luer member 110a to provide secure fluid communication between medical connector 100a and luer connector 38.

Figure 14:
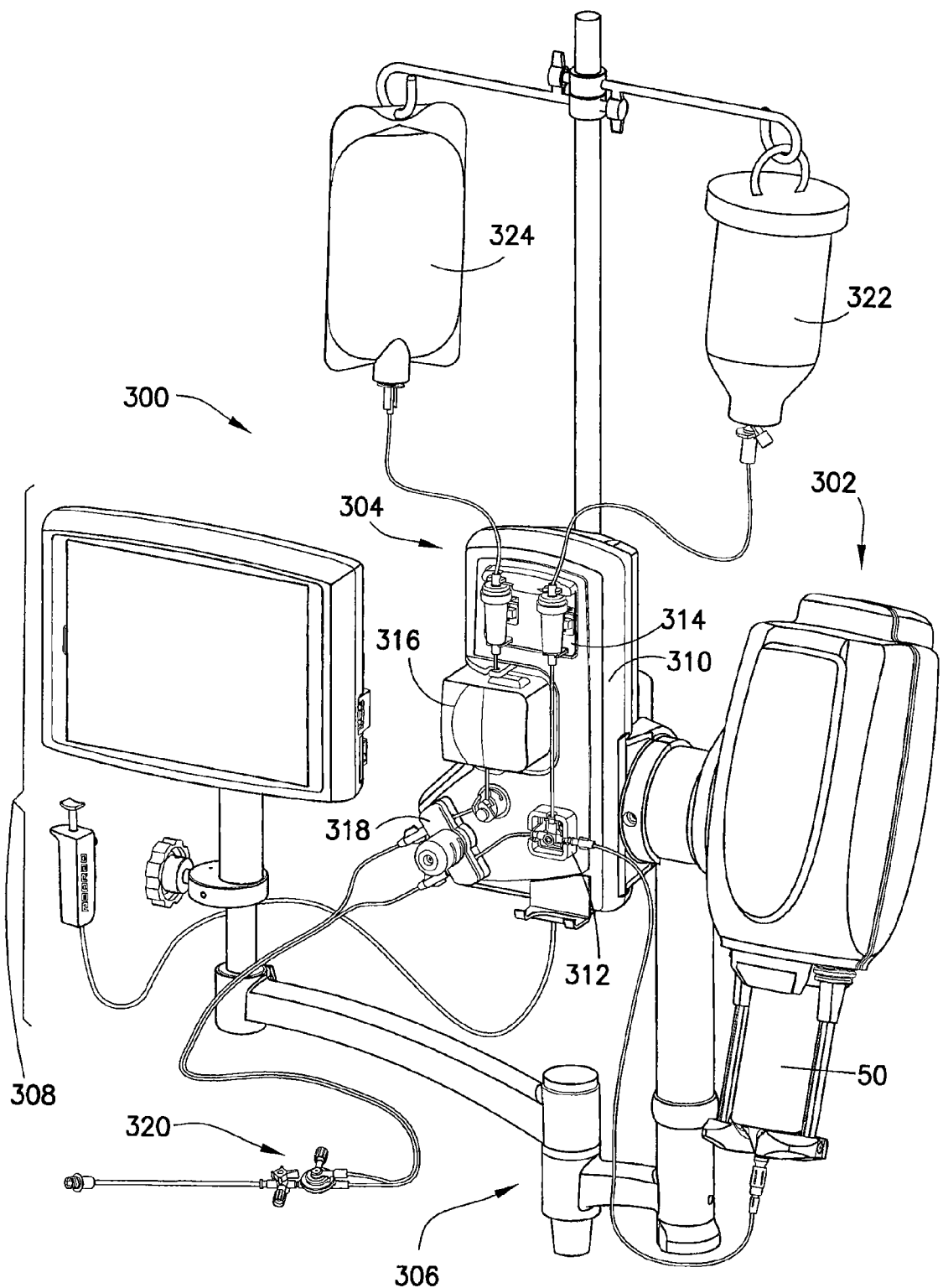
FIG. 14 is a perspective view of a fluid delivery system in which the various medical connectors provided in accordance with the present invention may be utilized.
Figure 15:
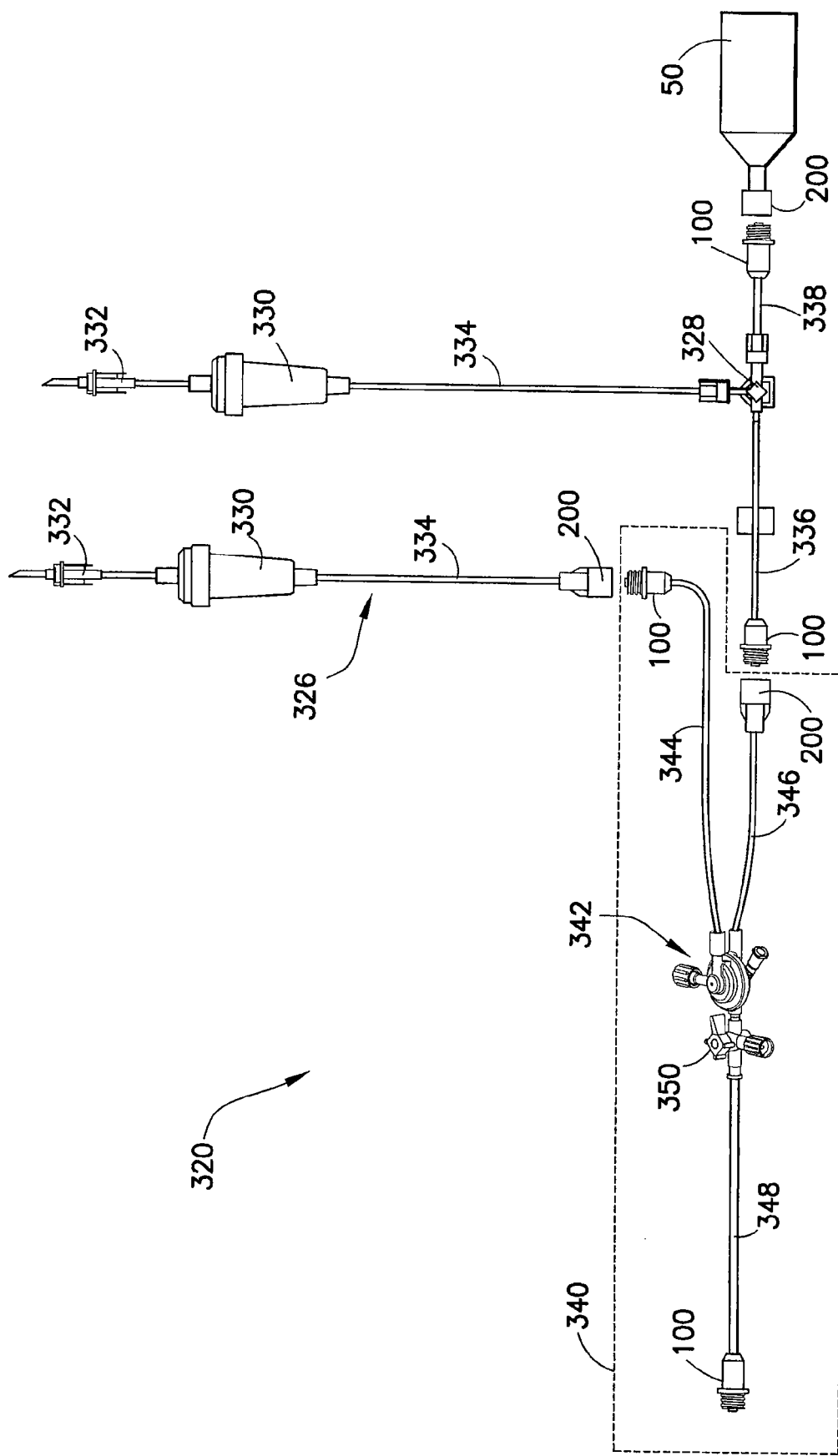
FIG. 15 is a top view of a fluid path adapted for use in the fluid delivery system of FIG. 14 and incorporating one or more of the medical connectors provided in accordance with the present invention.

One possible application of mating medical connectors 100, 200 is shown in FIGS. 14 and 15. FIG. 14 illustrates a fluid delivery system 300 that utilizes a fluid path 320 which comprises medical connectors 100, 200. Fluid delivery system 300 generally comprises an injector 302 operatively associated with a fluid control module 304, both of which are supported on a support structure 306. The details of injector 302 are provided in U.S. patent application Ser. No. 10/818,477, filed Apr. 5, 2004, entitled "Fluid Injection Apparatus with Front Load Pressure Jacket System with Syringe Holder and Light Illumination", and previously incorporated herein by reference in its entirety. The injector 302 is adapted to support and actuate a syringe, such as syringe 50 described previously. The fluid control module 304 is associated with injector 302 for controlling fluid flows delivered by the injector 302. The fluid control module 304 is generally adapted to support and control fluid path 320 used to connect the syringe associated with the injector 302 to a catheter, such as catheter 30 described previously. The details of fluid control module 304 are provided in U.S. patent application Ser. No. 10/826,149, filed Apr. 16, 2004 and entitled "Fluid Delivery System, Fluid Path Set, Sterile Connector and Improved Drip Chamber and Pressure Isolation Mechanism", assigned to the same assignee as the present application and which is incorporated herein by reference in its entirety.

The components of fluid delivery system 300 are supported by support assembly 306. Support assembly 306 may be configured as a movable platform or base so that fluid delivery system 300 is generally transportable, or for connection to a standard hospital bed or examination table on which a patient will be located during an injection procedure. Additionally, fluid delivery system 300 includes a user-input control section or device 308 or interfacing with computer hardware/software (i.e., electronic memory) of fluid control module 304 and/or injector 302. Fluid control module 304 generally comprises a housing 310, a valve actuator 312 for controlling a fluid control valve, a fluid level sensing mechanism 314, a peristaltic pump 316, and an air detector assembly 318. As indicated, fluid control module 304 is generally adapted to support and control fluid path 320.

Fluid path 320 is typically prepackaged as a "set" and typically comprises syringe 50 as part of the "set". Fluid path 320 is generally used to associate syringe 50 with a first or primary source of injection fluid 322, for example contrast, which will be loaded into syringe 50 for an injection procedure. Fluid path 320 is further adapted to associate fluid control module 304 with a secondary or additional source of typically flushing fluid 324 such as saline which is commonly supplied to a patient between injections of contrast in, for example, an angiography procedure. In a general injection procedure involving fluid delivery system 300, injector 302 is filled with fluid from the fluid container 322 and delivers the fluid via fluid path 320 to a catheter and, ultimately, the patient. Fluid control module 304 generally controls or manages the delivery of the injection fluid through a valve associated with the fluid path 320, which is controlled or actuated by valve actuator 312 on fluid control module 304. Fluid control module 304 is further adapted to deliver the fluid from secondary fluid container 324 under pressure via peristaltic pump 316.

Fluid path 320 generally comprises a first section or set 326 and a second section or set 340. The first section 326 is generally adapted to connect syringe 50 to primary fluid container 322, and to connect second section 340 to secondary fluid container 324. First section 340 is typically a multi-patient section or set disposed after a preset number of injection procedures are accomplished using fluid delivery system 300. Thus, first section 326 may be used for a preset number of injection procedures involving one or more with patients and may then be discarded. Optionally, but less desirably, first section 326 may be adapted to be re-sterilized for reuse. First section 326 is typically provided as a sterile set in a sterile package. Second section 340 is a per-patient section or set, which is typically disposed of after each injection procedure involving fluid delivery system 300. The first section 326 and second section 340 are placed in fluid communication by one or more of medical connectors 100, 200 the details of which were set forth previously.

First section 326 includes a multi-position valve 328, for example, a 3-position stopcock valve, which is adapted to be automatically controlled or actuated by valve actuator 312 on fluid control module 304. Multi-position valve 328 is adapted to selectively isolate syringe 50, primary fluid container 322, and second section 340 to selectively allow injector 302 to fill syringe 50 with fluid from primary fluid container 322, deliver fluid loaded into syringe 50 to second section 340, or isolate syringe 50 from primary fluid container 322 and second section 340. First section 326 further includes intervening drip chambers 330 associated with primary fluid container 322 and secondary fluid container 324. Drip chambers 330 are adapted to be associated with primary and secondary fluid containers 322, 324 with conventional spike members 332. Fluid level sensing mechanism 314 on fluid control module 304 is used to sense fluid levels in drip chambers 330 when fluid path 320 is associated with injector 300 and fluid control module 304. Generally, operation of fluid delivery system 300 includes filling, loading, or "priming" syringe 50 with fluid from primary fluid container 322, which passes to syringe 50 via the drip chamber 330 associated with primary fluid container 322. Similarly, during operation of fluid delivery system 300, fluid such as saline, from secondary fluid container 324 is supplied to second section 340 via the drip chamber 330 associated with secondary fluid container 324. The drip chambers 330 are generally adapted to permit fluid level sensors associated with fluid level sensing mechanism 314 to detect the level of fluid in drip chambers 330, for example, by using optical or ultrasonic methods. Respective output lines 334 made, for example, of conventional low pressure medical tubing, are associated with drip chambers 330 for connecting drip chambers 330 to multi-position valve 328 and second section 340. The outlet of the multi-position valve 328 is connected to an output line 336, which is used to connect multi-position valve 328 and syringe 50 to second section 340. Due to the high injection pressures typically generated by injector 302 during an injection procedure such as angiography, output line 336 is preferably constructed of high pressure medical tubing. An inlet to the multi-position valve 328 is connected via an inlet line 338 to syringe 50 which is also preferably constructed of high pressure medical tubing. A medical connector 100 is provided at the end of inlet line 338 to engage mating medical connector 200 at the distal or discharge outlet 68 (see FIG. 8A) of syringe 50 to place multi-position valve 328 in fluid communication with syringe 50. While medical connector 200 is shown associated with syringe 50 and medical connector 100 is shown associated with inlet line 338, this configuration may be reversed if desired. Accordingly, syringe 50 may alternatively have medical connector 100 disposed at the end of discharge outlet 68 of syringe body 52 as shown in FIG. 6, and medical connector 200 may be provided at the end of inlet line 338. Due to the relatively high pressures generated by operation of syringe 50 during, for example, angiographic procedure, medical connector 200 is preferably formed to form a "double-threaded" engagement with mating medical connector 100 as illustrated in FIG. 9C discussed previously.

Second section 340 generally includes a pressure isolation mechanism or valve 342. The pressure isolation mechanism 342 is connected by respective input lines 344, 346 and mating medical connectors 100, 200 to first section 326. First input line 344 is preferably formed of conventional medical tubing and connects pressure isolation mechanism 342 with the drip chamber 330 associated with secondary fluid container 324. Second input line 346 is preferably formed of high pressure medical tubing and connects pressure isolation mechanism 342 with output line 336 connected to multi-position valve 328 and, ultimately, syringe 50 and primary fluid container 22. The medical tubing used for second input line 346 is preferably high pressure medical tubing. While medical connector 100 is shown disposed at the end of output line 336 from multi-position valve 328 in first section 326 of fluid path 320 and mating medical connector 200 is shown disposed at the end of input line 346 to pressure isolation mechanism 342, this configuration may be reversed if desired. A similar reversal of mating medical connectors 100, 200 may be accomplished with the medical connector 200 disposed at the end of output line 334 from saline drip chamber 330 and mating medical connector 100 at the end of first input line 344 to pressure isolation mechanism 342. However, since second input line 346 and output line 336 associated with pressure isolation mechanism 342 and multi-position valve 328, respectively, are high pressure lines, typically comprised of high pressure medical tubing to withstand the high fluid pressures generated by syringe 50, medical connector 200 associated with either second input line 346 or output line 336 is preferably provided to form a "double-threaded" engagement with mating medical connector 100 as illustrated in FIG. 9C discussed previously.

An output line 348 is associated with pressure isolation mechanism 342 for connecting pressure isolation mechanism 342 with a catheter (not shown). A second multi-position valve 350, for example, in the form of a stopcock valve, may be provided in output line 348 as a shut-off feature. Output line 348 may further include a catheter connection, for example, medical connector 100, for associating fluid path 320 with a catheter. As will be appreciated from the foregoing discussion, such a catheter may alternatively be in the form of catheter 30 shown in FIG. 5 and, thus, medical connector 100 may be associated with catheter 30 rather than output line 348. As a result, medical connector 200 may be disposed at the end of output line 348 rather medical connector 100. In either configuration, medical connector 200 is preferably provided to form a "double-threaded" engagement with mating medical connector 100 as illustrated in FIG. 9C, to form a secure engagement between catheter 30 and second section 340 of fluid path 320.

As discussed previously, due to the presence of both internal and external threads 120, 122 on annular member 112 of medical connector 100, medical connector 100 is uniquely adapted to engage both an internally-threaded connector such as mating medical connector 200 or an externally-threaded luer connector such as conventional luer connectors 38, 70 associated with catheter 30 and syringe 50 shown in FIGS. 3A-3B and 4A-4B, respectively. Thus, medical connectors 200 shown in the first and second sections 326, 340 of fluid path 320 in FIG. 15 may alternatively be provided in the form of luer connectors 38, 70 if desired, which are still capable of mating with medical connectors 100 in FIG. 15.

Figure 16:
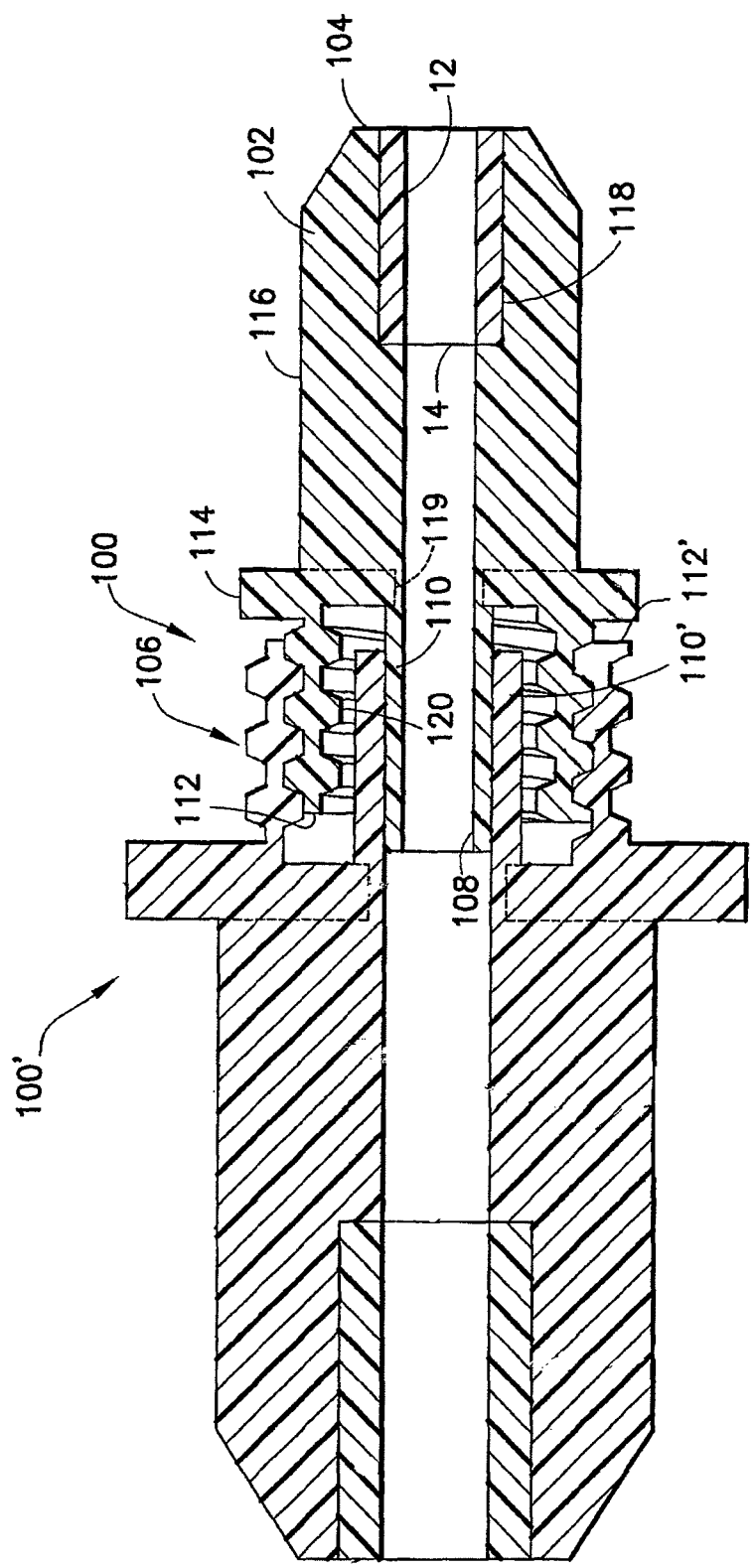
FIG. 16 is a cross-sectional view showing a mating engagement between two differently-sized medical connectors similar to the medical connector shown in FIG. 1 and comprising cooperating luer members.

Moreover, as shown in FIG. 16, it is even possible in accordance with the present invention to provide two mating medical connectors 100, 100' in which the medical connectors 100, 100' are differently-sized to cooperate with one another and comprise oppositely configured luer members 110, 110'. For example, one mating medical connector 100' may comprise an annular member 112' sized to receive the annular member 112 of a mating medical connector 100 configured in the manner shown in FIG. 2. The "receiving" medical connector 100' may comprise a "female" luer member 110' adapted to receive male luer member 110 associated with the "inserting" medical connector 100. As will be clear from the foregoing disclosure, the male-female configuration of luer members 110, 110' shown in FIG. 16 may be reversed if desired. Additionally, mating medical connectors 100, 100' may be provided in place of medical connectors 100, 200 in the fluid delivery system 300 and fluid path 320 of FIGS. 14 and 15, if desired.

Figure 17A:
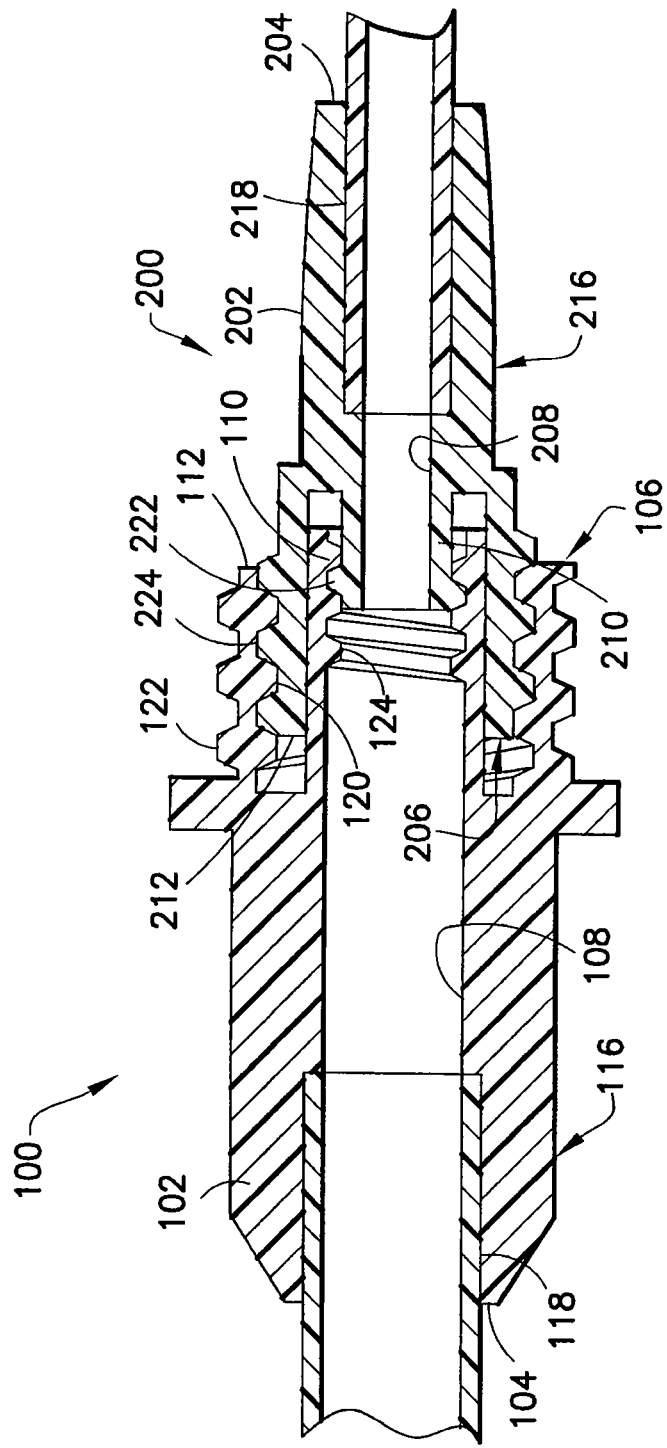
FIG. 17A is a cross-sectional view showing a variation of the medical connector of FIG. 1 engaged with a variation of the mating medical connector shown in FIGS. 7B and 8B.
Figure 17B:
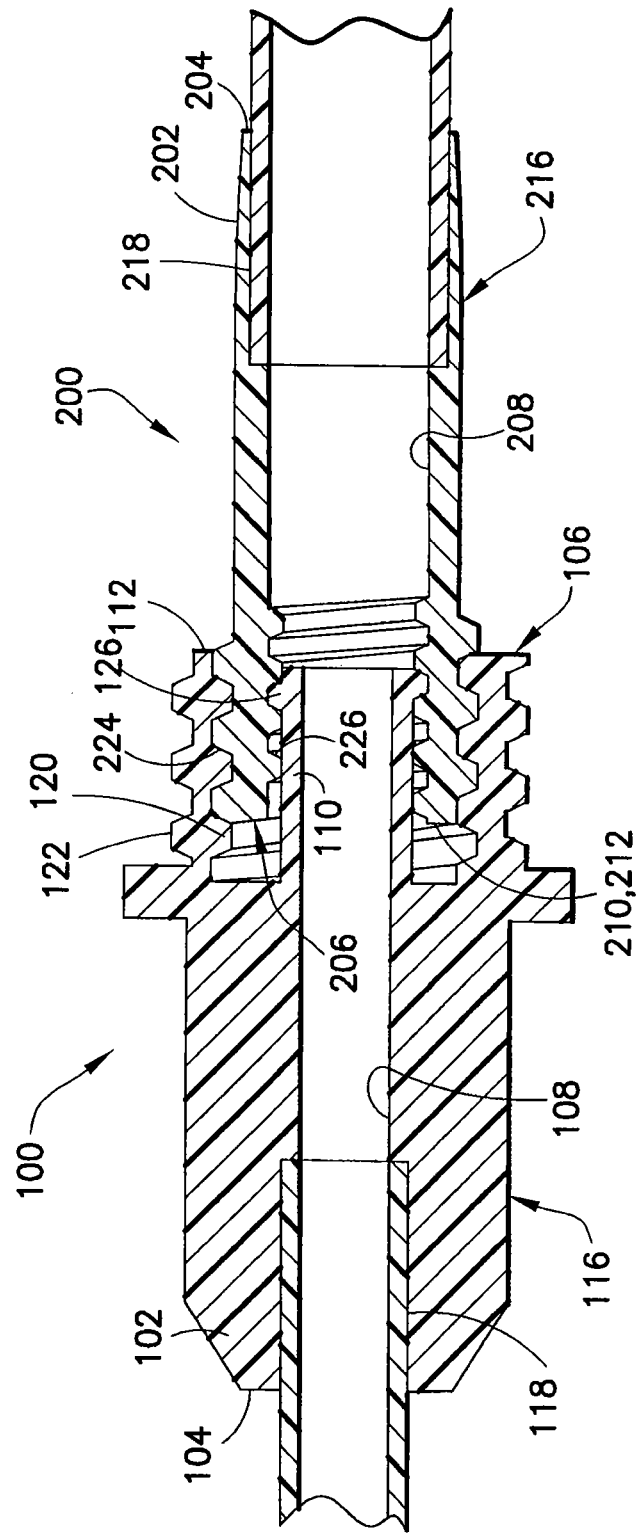
FIG. 17B is a cross-sectional view showing a second variation of the medical connector of FIG. 1 engaged with a second variation of the mating medical connector shown in FIGS. 7B and 8B.
Figure 17C:
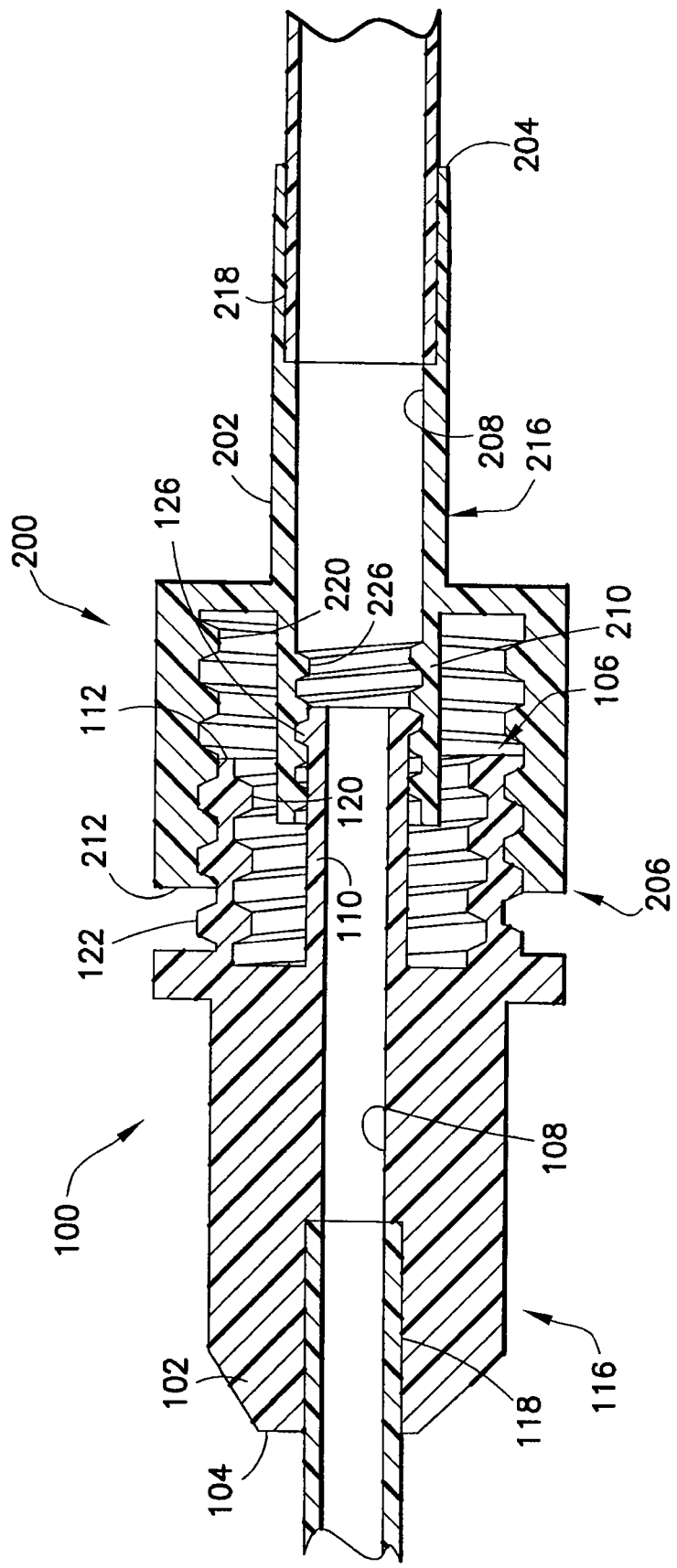
FIG. 17C is a cross-sectional view showing a third variation of the medical connector of FIG. 1 engaged with a third variation of the mating medical connector shown in FIGS. 7B and 8B.

Finally, FIGS. 17A-17C are cross-sectional views showing alternative variations of medical connectors 100, 200 which are adapted form a "doubled-threaded" engagement therebetween. In FIG. 17A, medical connector 100 comprises an annular member 112 formed in generally the same manner described previously in this disclosure comprising internal threads 120, but is now sized (e.g., enlarged) to receive the mating annular member 212 of medical connector 200. Annular member 212 of medical connector 200 is correspondingly now formed with external engagement structure 224, typically threads, in place of (or in addition to) internal threads 220 for establishing a threaded engagement with internal threads 120 in annular member 112 of medical connector 100. Luer member 210 of medical connector 200 still includes threaded flange 222 at the distal end thereof as described previously in connection with medical connector 200. However, luer member 110 of medical connector 100 shown in FIG. 17A now comprises internal engagement structure 124, typically threads, for establishing a threaded engagement with threaded flange 222 on luer member 210 of medical connector 200. Accordingly, the "double-threaded" connection between mating medical connectors 100, 200 in FIG. 17A comprises a threaded engagement between external threads 224 on annular member 212 of medical connector 200 and internal threads 120 on annular member 112 of medical connector 100, and a second threaded engagement between threaded flange 222 on luer member 210 of medical connector 200 and the internal threads 124 within luer member 110 of medical connector 100.

FIG. 17B shows a further variation of the "double-threaded" connection between mating medical connectors 100, 200. In FIG. 17B, medical connector 100 again comprises an annular member 112 sized (e.g., enlarged) to receive the mating annular member 212 of medical connector 200, and annular member 212 of medical connector 200 is again correspondingly formed with external threads 224 for establishing a threaded engagement with internal threads 120 in annular member 112 of medical connector 100. However, luer member 210 and annular member 212 are now desirably formed as an integral, unitary structure. Additionally internal luer member 110 of medical connector 100 now comprises an externally-threaded flange 126 at the distal end thereof in an analogous manner to threaded flange 222 on luer member 210 of medical connector 200 shown in FIG. 17A. Further, luer member 210 of medical connector 200 shown in FIG. 17B comprises internal engagement structure 226, typically threads, for establishing a threaded engagement with threaded flange 126 on luer member 110 of medical connector 100. Accordingly, the "double-threaded" connection between mating medical connectors 100, 200 in FIG. 17B comprises a threaded engagement between external threads 224 on luer/ annular member 210, 212 of medical connector 200 and internal threads 120 on annular member 112, and a second threaded engagement between threaded flange 126 on luer member 110 of medical connector 100 and the internal threads 226 within the luer/ annular member 210, 212 of medical connector 200.

Finally, FIG. 17C shows another variation of the "double-threaded" connection between mating medical connectors 100, 200. In FIG. 17C, annular member 212 of medical connector 200 is generally in the form described previously in this disclosure (FIGS. 7A, 8A as examples), wherein annular member 212 is adapted to receive the annular member 112 of medical connector 100 and form a threaded engagement with annular member 112. Accordingly, annular member 212 comprises internal threads 220 for forming a threaded engagement with external threads 122 on annular member 112 of medical connector 100. The threaded connection between luer members 110, 210 of medical connectors 100, 200 shown in FIG. 17C is generally similar to the threaded connection between these elements shown in FIG. 17B. In FIG. 17C, luer member 110 comprises threaded flange 126 at the distal end thereof, and luer member 210 comprises internal threads 226 for establishing a threaded engagement with threaded flange 126. The "double-threaded" connection between mating medical connectors 100, 200 in FIG. 17C now comprises a threaded engagement between external threads 122 on annular member 112 of medical connector 100 and internal threads 220 within annular member 212 of medical connector 200, and a second threaded engagement between threaded flange 126 on luer member 110 of medical connector 100 and the internal threads 226 within the luer member 210 of medical connector 200.

While the present invention was described with reference to several distinct embodiments of a fluid delivery system, fluid path, and medical connectors and medical connector assemblies therefor, those skilled in the art may make modifications and alterations to the present invention without departing from the scope and spirit of the invention. Accordingly, the above-detailed description is intended to be illustrative rather than restrictive. The invention is defined by the appended claims, and all changes to the invention that fall within the meaning and range of equivalency of the claims are to be embraced within their scope.

The invention claimed is:

1. A two-part medical connector, consisting essentially of:
a first part having a body defining a lumen for high pressure fluid flow through the medical connector and comprising a luer member and an annular member connected to the body, the luer member comprising external engagement structure and the annular member comprising internal and external engagement structure, wherein each of the external engagement structure of the luer member and the internal and external engagement structure of the annular member are in parallel alignment, the luer member further comprising a luer proximal end and a luer distal end and the annular member further comprising a proximal wall, an annular wall having a proximal end connected to the proximal wall and a distal end defining an annular opening, the luer proximal end of the luer member being integrally formed with the proximal wall of the annular member and the luer distal end of the luer member being recessed within the annular member and proximal to the distal end of the annular member; and
a flange formed on and extending circumferentially about the body of the first part and located rearward of the annular member;
wherein the body of the first part is connected to a second part having a body defining a second annular member, the second annular member comprising internal and external engagement structure, wherein said external engagement structure of the second annular member mates with the internal engagement structure of the annular member of the body of the first part and said internal engagement structure of the second annular member mates with the external engagement structure of the luer member of the body of the first part, said first and second parts capable of delivering fluid to a patient when mated.

2. The two-part medical connector of claim 1 wherein the internal and external engagement structure on the annular member of the body of the first part comprises threads.

3. The two-part medical connector of claim 1 wherein the luer member of the body of the first part comprises either a male luer member or a female luer member.

4. The two-part medical connector of claim 1 wherein the external engagement structure on the luer member of the body of the first part comprises threads.

5. A syringe, comprising:
a syringe body comprising a cylindrical main body portion, a conical portion connected to the cylindrical main body portion, and a discharge outlet connected to the conical portion;
a two-part medical connector connected to the end of the discharge outlet and comprising a first part having a body defining a lumen for high pressure fluid flow through the medical connector and comprising a luer member and an annular member connected to the body, the luer member comprising external engagement structure and the annular member comprising internal and external engagement structure, wherein each of the external engagement structure of the luer member and the internal and external engagement structure of the annular member are in parallel alignment, the luer member further comprising a luer proximal end and a luer distal end and the annular member further comprising a proximal wall, an annular wall having a proximal end connected to the proximal wall and a distal end defining an annular opening, the luer proximal end of the luer member being integrally formed with the proximal wall of the annular member and the luer distal end of the luer member being recessed within the annular member and proximal to the distal end of the annular member; and
a flange formed on and extending circumferentially about the body of the first part of the medical connector and located rearward of the annular member;

wherein the body of the first part is connected to a second part having a body defining a second annular member, the second annular member comprising internal and external engagement structure, wherein said external engagement structure of the second annular member mates with the internal engagement structure of the annular member of the body of the first part and said internal engagement structure of the second annular member mates with the external engagement structure of the luer member of the body of the first part, said first and second parts capable of delivering fluid from the syringe to a patient when mated.

6. The syringe of claim 5 wherein the internal and external engagement structure on the annular member of the body of the first part comprises threads.

7. The syringe of claim 5 wherein the luer member of the body of the first part comprises either a male luer member or a female luer member.

8. The syringe of claim 5 wherein the external engagement structure on the luer member of the body of the first part comprises threads.

9. A two-part medical connector, comprising:
a first part and a second part,
the first part comprising:
a luer member having an external engagement structure; and
a first annular member having an internal engagement structure and an external engagement structure,
wherein each of the external engagement structure of the luer member and the internal and external engagement structure of the first annular member are concentrically aligned,
the second part comprising:
a second annular member having an internal engagement structure and an external engagement structure,
wherein the second part is connectable to the first part to form a fluid delivery path by engaging at least one of the external engagement structure of the luer member, the external engagement structure of the first annular member, and the internal engagement structure of the second annular member.

10. The two-part medical connector of claim 9, wherein the first part and the second part are connectable by mating the external engagement structure of the second annular member of the second part with the internal engagement structure of the first annular member of the first part and mating the internal engagement structure of the second part with the external engagement structure of the luer member of the first part.

11. The two-part medical connector of claim 9, wherein each of the external engagement structure of the luer member and the internal and external engagement structure of the first annular member of the first part are of a different size.

12. The two-part medical connector of claim 9, wherein the luer member of the first part further comprises a luer proximal end and a luer distal end and the first annular member of the first part further comprises a proximal wall, an annular wall having a proximal end connected to the proximal wall and a distal end defining an annular opening, the luer proximal end of the luer member being integrally formed with the proximal wall of the first annular member.

13. The two-part medical connector of claim 12, wherein the luer distal end of the luer member of the first part is recessed within the first annular member and proximal to the distal end of the first annular member.

14. The two-part medical connector of claim 9, further comprising a flange formed on and extending circumferentially about each of the first and second annular members.

* * * * *

UNITED STATES PATENT AND TRADEMARK OFFICE
CERTIFICATE OF CORRECTION

PATENT NO. : 8,852,167 B2  
APPLICATION NO. : 11/426348  
DATED : October 7, 2014  
INVENTOR(S) : Trombley, III et al.

Page 1 of 1

It is certified that error appears in the above-identified patent and that said Letters Patent is hereby corrected as shown below:

IN THE SPECIFICATION:
Column 13, Line 35, delete "member 100a" and insert -- member 110a --, therefor.
Column 14, Line 11, delete "eternally-threaded" and insert -- externally-threaded --, therefor.
Column 14, Line 43, delete "&tined" and insert -- formed --, therefor.
Column 15, Line 31, delete "member 210" and insert -- member 212 --, therefor.
Column 16, Line 37, delete "member 210" and insert -- member 212 --, therefor.
Column 16, Line 38, delete "member 120a" and insert -- member 112a --, therefor.
Column 19, Line 32, delete "container 22." and insert -- container 322. --, therefor.
Column 20, Line 36, delete "adapted form" and insert -- adapted to form --, therefor.

Signed and Sealed this
Twenty-second Day of September, 2015

Michelle K. Lee
*Director of the United States Patent and Trademark Office*